US009120864B2

(12) United States Patent
Kardailsky et al.

(10) Patent No.: US 9,120,864 B2
(45) Date of Patent: Sep. 1, 2015

(54) FLOWERING INHIBITION

(75) Inventors: Igor Kardailsky, Ashhurst (NZ); Bruce Edward Veit, Ashhurst (NZ); Natasha Talei Forester, Rokomaru (NZ); Milan Gagic, Palmerston North (NZ); Kim Archer Richardson, Palmerston North (NZ); Martin John Faville, Palmerston North (NZ)

(73) Assignees: Agricultural Victoria Services PTY LTD, Attwood, Victoria (AU); AgResearch Limited, Hamilton (NZ)

( * ) Notice: Subject to any disclaimer, the term of this patent is extended or adjusted under 35 U.S.C. 154(b) by 993 days.

(21) Appl. No.: 10/557,031

(22) PCT Filed: May 14, 2004

(86) PCT No.: PCT/AU2004/000634
§ 371 (c)(1),
(2), (4) Date: Apr. 6, 2006

(87) PCT Pub. No.: WO2004/101792
PCT Pub. Date: Nov. 25, 2004

(65) Prior Publication Data
US 2007/0192904 A1 Aug. 16, 2007

(30) Foreign Application Priority Data

May 16, 2003 (AU) ................. 2003902412

(51) Int. Cl.
C12N 15/82 (2006.01)
C07K 14/415 (2006.01)
(52) U.S. Cl.
CPC ............ *C07K 14/415* (2013.01); *C12N 15/827* (2013.01)
(58) Field of Classification Search
USPC ....................................................... 800/290
See application file for complete search history.

(56) References Cited

U.S. PATENT DOCUMENTS

| | | | |
|---|---|---|---|
| 6,476,212 B1 | 11/2002 | Lalgudi et al. | |
| 2001/0051335 A1 | 12/2001 | Lalgudi et al. | |
| 2006/0070141 A1* | 3/2006 | Nielsen et al. ............... | 800/287 |

FOREIGN PATENT DOCUMENTS

| | | |
|---|---|---|
| EP | 1 342 765 | 9/2003 |
| WO | 97/10339 A1 | 3/1997 |
| WO | WO 99/49064 | 9/1999 |
| WO | 99/53070 | 10/1999 |
| WO | WO 01/26459 | 4/2001 |
| WO | WO 02/33091 | 4/2002 |
| WO | WO 02/44390 * | 6/2002 |
| WO | WO 03/000904 | 1/2003 |
| WO | WO 03/048319 | 6/2003 |
| WO | 2004022755 A3 | 3/2004 |

OTHER PUBLICATIONS

Jensen et al (Genbank Accession No. AF316419, 2001).*
Gyllenstrand et al., A Norway Spruce Flowering Locus T Homolog is Implicated in Control of Growth Rhythm in Conifers, 144 Plant Physiology, 248-257 at 24-250, 252-255 (2007).*
Laurie et al., The Medicago Flowering Locus T Homolog, MtFTa1, Is a Key Regulator of Flowering Time, 156 Plant Physiology, 2207-2224 at 2208, Left Column (2011).*
GenBank Accession No. CW347000; published Nov. 1, 2004.*
Cong et al., Genbank Accession No. AAD42896: Cen-like protein FDR2, 1999.
Park et al., Genbank Accession No. AAF00023: Gigantea [Arabidopsis thaliana], 1999.
Jenson et al., Genbank Accession No. AAG31808: A Terminal Flower1-like gene from perennial ryegrass involved in floral transition and axillary meristem identity, 2001.
Dunford et al., Genbank Accession No. AAL08497: gigantea-like protein [Hordeum vulgare], 2002.
Boss et al., Genbank Accession No. AAM46142: Terminal flower-like protein 1 (Vitis vinifera), 2002.
Taylor et al., Genbank Accession No. AF290457: Lolium perenne clonve PIB532, 2000.
Jensen et al., Genbank Accession No. AF316419: A Terminal Flower1-like gene from perennial rygrass involved in floral transition, 2001.
Dunfor et al., Genbank Accession No. AF411229: Hordeum vulgare gigantea-like protein, 2002.
Fowler et al., Genbank Accession No. AJ133787: Oryza sativa mRNA for gigantea homologue, partial, 1999.
Kojima et al., Genbank Accession No. BAB61027: Hd3a, a quanitative traitlocus, involves in the promotion of flowering in rice, Mar. 21, 2002.
Fowler et al, Genbank Accession No. CAB56058: gigantea homologue [Oryza saliva], 1999.
Muenster et al., Genbank Accession No. CAD23409: putative MADS-domain transcription factor [Zea mays], 2002.
Muenster et al., Genbank Accession No. CAD23439: putative MADS-domain transcription factor [Zea mays], 2002.

(Continued)

*Primary Examiner* — Ashwin Mehta
*Assistant Examiner* — Rebecca Stephens
(74) *Attorney, Agent, or Firm* — Larson & Anderson, LLC

(57) ABSTRACT

The present invention relates to nucleic acids or nucleic acid fragments encoding amino acid sequences for proteins involved in the control of flowering in plants, and the use thereof for the modification of flowering, particularly inhibiting flowering. In particular, the present invention relates to nucleic acids or nucleic acid fragments encoding amino acid sequences of FLOWERING LOCUS T (FT), TERMINAL FLOWER (TFL), GIGANTEA (GI) and SHORT VEGETATIVE PHASE (SVP) polypeptides.

11 Claims, 27 Drawing Sheets

(56) References Cited

OTHER PUBLICATIONS

Shinozuka et al., Genbank Accession No. BAA81880: MADS box-like protein [Oryza sativa (japonica cultivar-group)], Mar. 21, 2002.

Ohshima S. et al., Cloning and Molecular Analysis of the Arabidopsis Gene Terminal Flower 1, Molecular and General Genetics, 1997, pp. 186-194, vol. 254, No. 2, Springer Verlag, Berlin, DE.

Richardson Kim et al. "Microprojectile bombardment transformation of perennial ryegrass (Lolium perenne) for manipulation of flowering behaviour." In Vitro Cellular and Developmental Biology Animal. 2002. p. 80. A, vol. 38, Number Abstract.

Izawa T et al. "Phytochrome mediates the external light signal to repress FT orthologs in photoperiodic flowering of rice." Genes and Development, Cold Spring Harbor Laboratory Press. Aug. 1, 2002. pp. 2006-2020, vol. 16, No. 15.

Database EMBL. Oriza sativa Hd3a mRNA. Jun. 21, 2001. Abstract XP002381542.

Jensen C S et al. "A Terminal Flower1-like gene from perennial ryegrass involved in floral transition and axillary meristem identity." Plant Physiology, American Society of Plant Physilogoists. 2001. pp. 1517-1528, vol. 125, No. 3.

\* cited by examiner

```
>rgft2.seq
TGTATCTTTTGGGACTGAGGTTGTGTGCTACGAGAGCCCTCGGCCGGTGCTCGGGATCCACCGGCTGGT
GTTTCTGCTCT
TCCAACAGCTCGGCCGTCAGACCGTYTACGCTCCGGGCTGGCGGCAGAATTTCAGCACCCGCGACTTCG
CCGAGCTGTAC
AACCTCGGCTCGCCGGTCGCCGCCGTCTACTTCAACTGCCAAAGGGAGTCGGGAACTGGTGGAAGGAGG
ATGTGAATTCT
CTGACACTAGTCGTCAACCCGTGCGCCTGCACAGGCTAGTAATTGGTGAAATCGAATCATGGAGCCAAA
AAGGAGTTGTT
TCCAAATTTAATTGTGAAAATGGTTTTGATTTTCATtatatatagaattatatttAAAAAAAAAAAAAA
Aaaa >rgft1.seq
TGTATCTTTTGGGACTGAGGTTGTGTGCTACGAGAGCCCTCGGCCGGTGCTCGGGATCCACCGGCTGGT
GTTTCTGCTCT
TCCAACAGCTCGGCCGTCAGACCGTTTACGCTCCGGGCTGGCGGCAGAATTTCAGCACCCGCGACTTCG
CCGAGCTGTAC
AACCTCGGCTCGCCGGTCGCCGCCGTCTACTTCAACTGCCAAAGGGAGTCGGGAACTGGTGGAAGGAGG
ATGTGAATTCT
CTGACATATTATGACCATATAGGTTGAGCGTGGATGATTGTATCGGGGGTTATACGTGGCTAAATGAAA
AAAGATCATTG TAATAAAAAAAAAAAAAaa >rgmft.seq
GGTAAATTCTACTCATTGTGTATGACTGATCCGGCCGCACCGAGCAGGAAAGAACCTAAATTCAGGGAA
TGGCATCATTG
GCTCGTAGGCAATGTCCCAGAATGTGATGTAGCCAAGGGCGAAACTTTATCCGAATATATTGGCTCTGG
ACCTCCCCCAG
ATACTGGACTTCATCGTTATGTTTTCCTCGTCTACCTTCAGCCGGGTAAAATCGATTTCAAAGATGTGC
CACGTTTGACC
AACAGATCTGGTGACAATCGTGCCAATTTTAAAATTCAAGCTTTCGCCGATAAATATAATTTGGGCGAT
CCGGTGGCCTC
AGCTTATTATCGAGCCGAATACGACGACTACGTGCCAATTTTGTACAAACAATTGGGAGCA
```

FIGURE 1

>rgtfl1-2.seq
GCAGCAGCACATACACAATTACCTGAGCTTCCATTCAGCAAAGAGGAACACACGCACACTGATCATCCC
TCGGGTTCCGA
TTTCAAGGCATCAACATGTCAAGGGCGTTGGAGCCTCTCGTTGTGGGGAAGGTGATTGGTGAGGTGCTG
GACAGCTTCAA
CCCCACCGTGAAGATGACGGCAACCTACAGCTCCAACAAGCAGGTGTTCAACGGCCATGAGTTCTTCCC
CTCGGCCATCG
CCGCTAAGCCGCGTGTCGAGGTTCAGGGGGGCGACCTTAGATCCTTCTTCACATTGGTGATGACTGACC
CTGATGTGCCA
GGACCCAGTGATCCGTACCTGAGGGAGCATCTTCACTGGATTGTTACTGATATTCCTGGGACTACTGAT
GCTTCTTTTGG
GAAGGAGGTGGTGCACTACGAGAGCCCAAAGCCAAACATCGGCATCCACAGGTTCATCCTCGTGCTGTT
CCAGCAGACGC
ACCGGGGCTCGGTAAAGAACACACCGTCGTCGAGGGACCGCTTCAGGACCCGCGAGTTCGCCAAGGATA
ACGAGCTCGGC
CTCCCTGTCGCYGCTGTCTACTTCAACGCGCAGCGGGAGACCGCCGCCCGCCGGCGATAGCTCAACGGC
AACCGAACCAA
CCAACCAGCAACACCCCCCTACTATGTACCTGATCTAGCTACATGATAAAACGAACTGCGTACAATCAC
CTATTAGCTAG
CTTCGATGGCCTTTCCTGCTACATCCAAGCATGCACAATGTCTGAATAAAACACACCGGTAAATTAGCT
GTTTGCACGAG
AAAGCTGCTCCYTACTAGTACGTAGCCGTTGCCCATTTAGTTAATTTTTGTGAATGTGACAAGATCGAT
GATTGGGAAGA
GATTGCAGTGTTGACTGAGAAAAAAGTGCAAGATTTGAAGCAATAATAGTCGTCAGGGAGTA------
AAAAAAAAAAA AAAAAAAAAA >rgtfl1-1.seq
AACAACCATGAGGTTATATTTCCTCATTCCTCAAGACTGTTTACCTAGTGCTTCGACTTGCTAGTTACC
TGTCAGCTGTA
GATATTTGGCATCGATCATCACCACCTTTTCAGTTCAAGTTAGCTAGCTAGACATGGCTAGGGTGGTGG
AGCCTCTCATC
GTCGGAAAGGTGATCGGGGAGGTCATCGACAACTTCACCCCCACTGAGAAGATGACAGTAACCTACAGC
TCCAACAAGCA
GGTGTTCAATGGCCACGAATTCTTCCCGTCGGCAGTCGTCTCCAAGCCACGCATTGAGGTCCAGGGTGG
CGACATGAGAT
CCTTCTTCACACTGGTCATGACGGACCCAGATGTGCCAGGGCCTAGCGACCCATACCTGAGGGAGCATC
TCCACTGGATC
GTCAATAATATTCCAGGCACCACTGATGCTTCTTTTGGAAAGGAGGTGGTGAGCTACGAGAGCCCCAAG
CCCAACATCGG
CATTCACAGGTTCACCTTCGTGCTGTTCAAGCAGAAGCAGCGGCAGACAATGAGCCCTCCCTCCAGCAG
GGACTACTTCA
ACACTCGCCGCTTCGCTGCCGCGAACGATCTTGGCCTCCCAGTCGCTGCCGTCTACTTCAACGCGCAGC
GGGAGACAGCT
GCGCGCCGCCGCTGATGGAAACAATCAGCGAAACCCTTCTTCTCGCGCATGCATGGCGCATGCATGCAA
TCCTATGGATC
AACCAATAGCTCTACTACTAGCTACCCTTTATGTCTTTCATTCAAATAAGAGTTTGCTTGTGAGCgtct
tgtgtcAAAAA AAAAAAAAAA

FIGURE 1 (cont.)

```
  1  TCGACTGGAG CACGAGGACA CTGACATGGA CTGAAGGAGT AGAAACCCCA ACCACGTTAC GGATGAAAAA

71  ATCTTTTTCT CGCCTCTCCT CGCCCCTCGC TCCAAGCTTC TCTCTCCTCG CCGTCTACCG CTCGCCGCCG
                                                                             M  X  .

141  CCGCTGATTC GCCGCCGGAG CCACGGAGTA GAGCGCGCCC AGTCTAGGAT CTTAAACTAA TAAGTATGYC
     .  V  S  N  G  K  W  I  D  G  L  Q  F  S  S  L  F  W  P  P  P  H  D  A

211  TGTCTCAAAT GGGAAGTGGA TCGACGGGCT CCAGTTCTCT TCACTATTCT GGCCCCCGCC ACACGATGCA
     Q  Q  K  Q  A  Q  T  L  A  Y  V  E  Y  F  G  Q  F  T  S  D  S  E  Q  F  .

281  CAGCAGAAAC AGGCACACAA CTTTGGCCTAC GTTGAGTACT TTGGTCAGTT TACATCTGAC AGTGAGCAAT
     .  P  E  D  V  A  Q  L  I  Q  S  Y  Y  P  S  K  E  K  R  L  V  D  E  V  .

351  TCCCGGAGGA TGTAGCTCAG CTCATCCAAA GTTACTATCC ATCGAAAGAA AAACGCTTGG TAGATGAAGT
     .  L  A  T  F  V  L  H  H  P  E  H  G  H  A  V  V  H  P  I  L  S  R  I

421  ATTAGCAACC TTTGTTCTCC ATCACCCCGA GCATGGTCAT GCAGTGTAC ATCCAATTCT TTCACGCATC
     I  D  G  S  L  S  Y  D  R  H  G  S  P  F  N  S  F  I  S  L  F  T  Q  T  .
```

FIGURE 3

```
491  ATAGATGGGT CCCTGAGTTA TGATAGACAT GGTTCCCCAT TCAATTCTTT CATCTCTTTA TTTACCCAAA
      .  A  E  K    E  Y  S    E  Q  W  A    L  A  C    G  E  I    L  R  V  L    T  H  Y

561  CTGCTGAGAA AGAGTATTCA GAGCAGTGGG CTTTGGCGTG TGGAGAAATT CTTAGAGTTC TTACTCACTA
      .  N  R  P    I  F  K  V    A  E  C    N  D  T    S  D  Q  A    T  T  S    Y  S  L

631  CAATAGGCCA ATCTTCAAAG TTGCAGAATG TAACGACACC TCCGACCAGG CCACAACAAG TTATTCCTTA
      H  D  K  A    N  S  S    P  E  N    E  P  E  R    K  P  L    R  P  L  S    P  W  I

701  CATGACAAAG CTAATAGCTC TCCAGAAAAT GAACCTGAAC GGAAGCCATT GAGGCCATTA TCTCCTTGGA
      .  T  D  I    L  L  N    A  P  L  G    I  R  S    D  Y  F    R  W  C  G    G  V  M

771  TCACAGACAT TTTGTTAAAT GCACCTTTGG GCATTAGAAG TGACTATTTT AGATGGTGTG GTGGAGTCAT
      .  G  K  Y    A  A  G  G    E  L  K    P  P  T    T  A  Y  S    R  G  A    G  K  H

841  GGGAAAATAC GCAGCTGGTG GAGAACTGAA GCCTCCAACA ACTGCTTACA GCCGGGGAGC TGGTAAGCAT
      P  Q  L  M    P  S  T    P  R  W    A  V  A  N    G  A  G    V  I  X  V    C  D  .
```

FIGURE 3 (cont.)

```
 911  CCACAACTTA TGCCATCCAC CCCTAGATGG GCTGTTGCCA ATGGAGCTGG AGTCATCWTA WGTGTCTGTG
       .  E  E  V   A  R  Y   E  T  A  N   L  T  A   A  A  V   P  X  L   L  P  P  .

981  ACGAGGAAGT AGCTCGTTAC GAGACAGCAA ACTTAACCGC AGCAGCTGTT CCTGSGCTTC TGCTACCTCC
       .  P  T  M   P  L  D  E   H  L  V   A  G  L   P  P  L  E   P  Y  A   R  L  F

1051  ACCGACAATG CCCTTGGATG AGCATTTGGT GGCAGGGGTG CCCCCTCTTG AACCATACGC TCGCTTGTTT
        H  R  Y  Y   A  I  A   T  P  S   A  T  Q  R   L  L  F   G  L  L   E  A  P  P  .

1121  CACAGATACT AYGCAATTGC TACTCCAAGT GCTACACARA GGTTGCTCTT TGGTCTTCTT GAAGCACCGC
       .  S  W  A   P  D  A   L  D  A  A   V  Q  L   V  E  L   L  R  A  A   E  D  Y  .

1191  CTTCATGGGC TCCAGATGCA CTTGATGCAG CAGTACAGCT TGTTGAACTC CTTCGAGCAG CCGAAGATTA
       .  A  T  G   M  R  L  P   K  N  W   L  H  L   H  F  L  R   A  I  G   T  A  M

1261  TGCTACTGGC ATGCGGGCTTC CGAAAAATTG GCTGCATCTT CATTTCTTGC GTGCAATCGG AACTGCAATG
        S  M  R  A   G  M  A   A  D  T   A  A  A  L   L  F  R   I  L  S   Q  P  T  L  .
```

FIGURE 3 (cont.)

```
1331 TCTATGAGAG CTGGYATGGC TGCTGATACG GCCGCTGCCT TGCTATTTCG TATACTATCC CAACCAACGT
     · L F P  P L R  H A E G  V V Q  H E P  L G G Y  V S S ·
     ~~~~~~~~~~~~~~~~~~~~~~~~~~~~~~~~~~~~~~~~~~~~~~~~~~~~~~~~~~~~~~~~~~~~~~~~~~~
1401 TGCTTTTTCC TCCACTAAGA CATGCCGAAG GAGTTGTGCA GCATGAACCA CTAGGTGGCT ATGTATCATC
     ·Y K R  Q L E I  P A S  E T T  I D A T  A Q G  I A S
     ~~~~~~~~~~~~~~~~~~~~~~~~~~~~~~~~~~~~~~~~~~~~~~~~~~~~~~~~~~~~~~~~~~~~~~~~~~~
1471 ATACAAAAGA CAGCTGGARA TTCCTGCATC TGAAACCACT ATTGATGCTA CTGCACAAGG CATTGCTTCC
     L L C A  H G P  D V X  W R I C  T I W  E A A  Y G L L ·
     ~~~~~~~~~~~~~~~~~~~~~~~~~~~~~~~~~~~~~~~~~~~~~~~~~~~~~~~~~~~~~~~~~~~~~~~~~~~
1541 TTGCTGTGYG CTCATGGTCC TGATGTTGAK TGGAGAATAT GTACCATCTG GGAAGCTGCC TATGGTTTGT
     · P L N  S S A  V D L P  E I V  V A A  P L Q P  P T L ·
     ~~~~~~~~~~~~~~~~~~~~~~~~~~~~~~~~~~~~~~~~~~~~~~~~~~~~~~~~~~~~~~~~~~~~~~~~~~~
1611 TACCTCTGAA TTCRTCAGCA GTCGATTTGC CTGAAATTGT TGTAGCTGCT CCGCTTCAGC CACCTACTTT
     ·S W S  L Y L P  L L K  V F E  Y L P R  G S P  S E A
     ~~~~~~~~~~~~~~~~~~~~~~~~~~~~~~~~~~~~~~~~~~~~~~~~~~~~~~~~~~~~~~~~~~~~~~~~~~~
1681 ATCATGGAGC CTATATTTGC CACTGTTGAA AGTATTTGAG TATCTACCTC GTGGAAGTCC ATCTGAAGCA
     C L M R  I F V  A T V  E A I L  R R T  F P S  E T E P ·
     ~~~~~~~~~~~~~~~~~~~~~~~~~~~~~~~~~~~~~~~~~~~~~~~~~~~~~~~~~~~~~~~~~~~~~~~~~~~
```

FIGURE 3 (cont.)

1751  TGCCTTATGA GAATATTTGT GGCAACTGTT GAAGCTATAC TCAGGAGAAC TTTCCCTTCG GAAACCGAAC
       .  S   K   K   P   R   S   P   S   K   S   L   A   V   A   E   L   R   T   M   I   H   S   L   .

1821  CATCCAAAAA ACCAAGAAGT CCATCTAAGA GCCTTGCTGT TGCTGAACTC CGTACGATGA TACATTCACT
       .  F   V   E   S   C   A   S   M   N   L   A   S   R   L   L   F   V   V   L   T   V   S   V

1891  CTTTGTTGAA TCATGTGCCT CAATGAACCT TGCTTCGCGG TTATTGTTTG TAGTATTGAC TGTCTCAGTC
       S   H   Q   A   L   P   G   G   S   K   R   P   T   G   S   E   N   H   S   S   E   E   S   T   .

1961  AGTCATCAAG CTCTGCCGGG GGGCAGCAAA AGACCTACAG GCAGTGAGAA CCATTCTTCT GAGGAGTCCA
       .  E   D   S   K   L   T   N   G   R   M   R   C   K   K   K   Q   G   P   V   G   T   F   D

2031  CTGAGGACTC AAAATTAACC AATGAAGAAA ACAGATGCAA GAAGAAACAA GGGCCTGTTG GTACCTTTGA
       .  S   Y   V   L   A   A   V   C   A   L   S   C   E   L   Q   L   F   P   I   L   C   K   N

2101  CTCGTATGTG CTGGCTGCTG TTTGTGCTTT ATCTTGTGAG CTTCAGCTGT TCCCTATACT TTGCAAGAAT
       V   T   K   T   N   I   K   D   S   I   K   I   T   M   P   G   K   T   N   G   I   S   N   E   .

2171  GTTACGAAGA CAAACATAAA AGACTCTATA AAGATTACCA TGCCTGGAAA AACCAATGGG ATCAGTAATG
       .  L   H   N   S   V   N   S   A   I   L   H   T   R   R   I   L   G   I   L   E   A   L   F   .

FIGURE 3 (cont.)

```
2241  AGTACACAA TAGCGTTAAC TCAGCGATTC TCCATACTCG TAGAATTCTT GGCATCCTGG AAGCTCTTTT
       . S  L  K   P  S  S   V  G  T   S  W  S   Y  S  S   N  E  I   V  A  A   A  M

2311  CTCCTTGAAG CCATCATCAG TTGGTACCTC CTGGAGCTAT AGTTCAAATG AGATAGTTGC AGCAGCAATG
        V  A  A   H  V  S   E  L  F   R  R  S   R  P  C   L  N  A   L  S  A   L  K  R  .

2381  GTTGCTGCTC ATGTTTCTGA GTTATTCCGT AGGTCGAGGC CATGCCTAAA TGCACTATCT GCACTGAAGC
       . C  K  W   D  A  E   I  S  T   R  A  S   S  L  Y   H  L  I   D  L  H   G  K   .

2451  GATGTAAGTG GGATGCTGAG ATTTCTACCA GGGCATCATC GCTTTACCAT CTGATCGACT TGCATGGTAA
       . T  V  S   S  I  V   N  K  A   E  P  L   E  A  H   L  N  L   T  A  V   K  K

2521  AACTGTGTCA TCCATCGTGA ACAAAGCTGA GCCTTTGGAA GCTCACCTGA ACCTTACAGC AGTAAAGAAA
        D  D  Q   H  H  I   E  E  S   N  T  S   S  S  D   Y  G  N   L  E  K   K  S  K  .

2591  GATGATCAAC ACCACATTGA GGAAAGCAAT ACCAGCTCAT CGGATTATGG GAACTTGGAG AAGAAGAGTA
       . K  N  G   F  S  R   P  L  M   K  C  A   E  Q  A   R  R  N   G  N  V   A  S   .

2661  AGAAAAATGG TTTTTCAAGA CCACTCATGA AATGTGCAGA ACAGGCTAGG AGAAATGGTA ACGTTGCAAG
       . T  S  G   K  A  T   A  T  L   Q  A  E   A  S  D   L  A  N   F  L  T   M  D
```

FIGURE 3 (cont.)

```
2731  TACATCGGGG AAAGCTACTG CAACTTTACA GGCGGAAGCA TCTGATTTGG CAAACTTCCT TACCATGGAC
       R  N  G  G  Y  G  G  S  Q  T  L  L  R  T  V  M  S  E  K  Q  E  L  C  F  .

2801  AGGAACGGGG GTTATGGAGG TTCTCAAACT CTCCTAAGAA CTGTAATGTC AGAAAAGCAG GAACTATGCT
       S  V  V  S  L  L  W  H  K  L  I  A  S  P  E  T  Q  M  S  A  E  S  T  .

2871  TTTCTGTTGT CTCGTTGCTG TGGCATAAGC TTATTGCATC TCCCGAAACA CAGATGTCTG CAGAGAGTAC
       S  A  H  Q  G  W  R  K  V  A  D  A  L  C  D  V  V  S  A  S  P  A  K

2941  ATCAGCTCAT CAGGGTTGGA GAAAGGTTGC AGATGCGCTT TGTGATGTTG TTTCAGCTTC ACCGGCCAAG
       A  X  T  A  I  V  L  Q  A  E  K  D  L  Q  P  W  I  A  R  D  D  E  Q  G  .

3011  GCTHCAACTG CTATTGTCCT GCAGGCTGAG AAGGACTTGC AGCCCTGGAT TGCTCGAGAT GATGAGCAAG
       Q  K  M  W  R  V  N  Q  R  I  V  K  L  I  A  E  L  M  R  N  H  D  S  .

3081  GTCAGAAGAT GTGGAGAGTC AACCAGCGAA TAGTGAAACT GATAGCTGAG CTTATGAGGA ACCATGATAG
       P  E  A  L  I  L  A  S  A  S  D  L  L  R  A  T  D  G  M  L  V

3151  CCCAGAAGCA CTGATAATTC TTGCGAGCGC TTCAGACCTT CTGCTCCGTG CCACGGATGG GATGCTTGTT
       D  G  E  A  C  T  L  P  Q  L  E  L  L  E  V  T  A  R  A  I  H  L  I  V  .
```

FIGURE 3 (cont.)

```
3221  GATGGTGAAG CTTGTACCTT GCCTCAATTG GAGCTTCTGG AAGTAACCGC CAGAGCCATT CATCTCATCG
       .  E  W  G   D  P  G   V  A  V   A  D  G   L  S  N   L  L  K  C   R  L  S  P  .

3291  TTGAATGGGG AGATCCAGGT GTAGCAGTTG CTGATGGCCT CTCGAATCTG CTGAAGTGCC GGCTATCACC
       .  T  I  R   C  L  S   H  P  S   A  H  V   R  A  L   S  M  S  V   L  R  D  I

3361  TACCATCCGA TGCCTTTCCC ACCCTAGTGC ACATGTACGG GCGCTCAGCA TGTCCGTCCT TCGCGACATC
       L  N  S  G   P  I  S   T  K  I   I  Q  G   E  Q  R   N  G  I  Q   S  P  S  .

3431  TTGAACAGTG GACCAATAAG TTCCACCAAG ATAATTCAAG GAGAGCAGCG GAACGGCATC CAAAGCCCAA
       .  Y  R  C   A  A  A   S  M  T   N  W  Q   A  D  V   E  R  C  I   E  W  E  A  .

3501  GTTACCGGTG CGCGGCAGCA AGTATGACCA ACTGGCAAGC GGACGTCGAG AGATGCATAG AGTGGGAAGC
       .  H  N  R   Q  A  T  G   M  T  L   A  F  L   T  A  A  A   N  E  L   G  C  P

3571  CCACAACCGT CAGGCCACCG GGATGACGCT TGCCTTTCTC ACTGCAGCKG CTAACGAACT CGGATGCCCC
       L  P  C  *

3641  CTTCCTTGCT GACACAGCCA TATTTGAAGC TGRCATCGGC GAYACTTGAC RGTTAGCGCG AGCAGTTGCT
3711  GCATGGTCAG CGAGCAGGAT GGCTAATCCY TKGCTCAAGG ATGACTTCCC AGTCTGAA
```

FIGURE 3 (cont.)

```
  1  AANTTGTACA   CGATTTCACT   ATAGTGGCGA   ATTGGGCCCT
     CTATATGCAT   GCTCGAGCGG   CCGCCAGTGT   GATGGATATC
     TGCAGAATTC

TTNAACATGT   GCTAAAGTGA   TATCACCGCT   TAACCCGGGA
     GATATACGTA   CGAGCTCGCC   GGCGGTCACA   CTACCTATAG
     ACGTCTTAAG

91  GGCCCTTTYM   TMYYYCTCCT   CTCCTTTCGC   ATCCCCAACC
     GCACCACTGT   GCCTCTCCGA   CCCCGGCCGG   CCGACGCGCG
     CTACGCCTCT

CCGGGAAARK   AKRRRGAGGA   GAGGAAAGCG   TAGGGGTTGG
     CGTGGTGACA   CGGAGAGGCT   GGGGCCGGCC   GGCTGCGCGC
     GATGCGGAGA

181  CGGCGTGDGG   ACTGGGGRGG   RRGGAGGAGA   KMGATCGATC
     RGTYGGGYYS   GGAGGCGGCG   ATGGCGCGGG   AGAGGCGCGA
     GATCAAGCGG

GCCGCACHCC   TGACCCCYCC   YYCCTCCTCT   MKCTAGCTAG
     YCARCCCRRS   CCTCCGCCGC   TACCGCGCCC   TCTCCGCGCT
     CTAGTTCGCC

271  ATAGAGAGCG   CGGCGGCGCG   CCAGGTCACC   TTCTCCAAGC
     GCCGCAGGGG   CCTCTTCAAG   AAGGCCGAGG   AGCTCTCCGT
     CCTATGCGAC
```

FIGURE 4a

```
    TATCTCTCGC  GCCGCCGCGC  GGTCCAGTGG  AAGAGGTTCG
    CGGCGTCCCC  GGAGAAGTTC  TTCCGGCTCC  TCGAGAGGCA
    GGATACGCTG

361 GCCGACGTCG  CGCTCATCGT  CTTCTCGTCC  ACAGGGAAGC
    TCTCCCAGTT  CGCAAGCTCC  AGTATGAATG  AGATCATCGA
    CAAGTACAGC

CGGCTGCAGC  GCGAGTAGCA  GAAGAGCAGG  TGTCCCTTCG
    AGAGGGTCAA  GCGTTCGAGG  TCATACTTAC  TCTAGTAGCT
    GTTCATGTCG

451 ACCCATTCTA  AGAACCTGGG  GAAAGCAGAC  CAGCCTTCTC
    TTGACTTGAA  TTTAGAACAT  AGTAAGTATG  CAAATCTGAA
    CGATCAGCTT

TGGGTAAGAT  TCTTGGACCC  CTTTCGTCTG  GTCGGAAGAG
    AACTGAACTT  AAATCTTGTA  TCATTCATAC  GTTTAGACTT
    GCTAGTCGAA

541 GCGGAAGCTA  GTCTYCGACT  TAGACAGATG  AGAGGCGAGG
    GGCTTGAGGG  GTTGAVTGTT  GATGAACTCC  AGCAGTTGGA
    GAAGAACCTT

CGCCTTCGAT  CAGARGCTGA  ATCTGTCTAC  TCTCCGCTCC
    CCGAACTCCC  CAACTBACAA  CTACTTGAGG  TCGTCAACCT
    CTTCTTGGAA
```

FIGURE 4a (cont.)

631  GAAACTGGTC  TGCACAGGGT  GCTTCAGACG  AAAGATCAAC
     AATTCTTGGA  GCAGATCAAT  GAATTGCAAC  GAAAGAGCTC
     ACAGCTGGCA

CTTTGACCAG  ACGTGTCCCA  CGAAGTCTGC  TTTCTAGTTG
     TTAAGAACCT  CGTCTAGTTA  CTTAACGTTG  CTTTCTCGAG
     TGTCGACCGT

721  GAGGAGAACA  TGCAACTGAG  GAACCAAGTA  TCCCAGATAC
     CAATAGCTGG  CAAGCCAGTA  GTTGCTGATA  CCGAAAATGT
     TATTGCTGAG

CTCCTCTTGT  ACGTTGACTC  CTTGGTTCAT  AGGGTCTATG
     GTTATCGACC  GTTCGGTCAT  CAACGACTAT  GGCTTTTACA
     ATAACGACTC

811  GATGGGCAGT  CCTCTGAATC  TGTCATGACG  GCGTTGCACT
     CGGGAAGCTC  ACAGGATAAC  GATGATGGTT  CAGATGTATC
     CCTGAAATTG

CTACCCGTCA  GGAGACTTAG  ACAGTACTGC  CGCAACGTGA
     GCCCTTCGAG  TGTCCTATTG  CTACTACCAA  GTCTACATAG
     GGACTTTAAC

901  GGATTACCCT  GCAGTGCGTG  GAAGTAACTA  TATAAAAYCG
     TCRSTTCAGA  TCTTTATGGA  ACTGCCCACR  TCAGTGGAGA
     AGCTCTTGTG

FIGURE 4a (cont.)

|      | | | | |
|------|---|---|---|---|
|      | CCTAATGGGA | CGTCACGCAC | CTTCATTGAT | ATATTTTRGC |
|      | AGYSAAGTCT | AGAAATACCT | TGACGGGTGY | AGTCACCTCT |
|      | TCGAGAACAC | | | |
| 991  | TAATCSACAA | ACGTACCYGA | GCTGCAATAA | TCTTGCRGCT |
|      | GAAGCGAGAT | CAGTTAACCT | GATTTATCAT | CCTTGTGGCT |
|      | GCATGACGTG | | | |
|      | ATTAGSTGTT | TGCATGGRCT | CGACGTTATT | AGAACGYCGA |
|      | CTTCGCTCTA | GTCAATTGGA | CTAAATAGTA | GGAACACCGA |
|      | CGTACTGCAC | | | |
| 1081 | ATGTTCCCGT | TYTTACYGTT | TACTAGGATG | TTAACTAAAC |
|      | TTTTAGATCG | ATCTGATGTC | CATCTTATCC | CCGTTGGCAC |
|      | TATTTGTTCA | | | |
|      | TACAAGGGCA | ARAATGRCAA | ATGATCCTAC | AATTGATTTG |
|      | AAAATCTAGC | TAGACTACAG | GTAGAATAGG | GGCAACCGTG |
|      | ATAAACAAGT | | | |
| 1171 | TGGTATCCAT | GTACCTTAAC | TGTCAGTATA | TCTTAAAMTT |
|      | ATGGTCTATA | WWTKCWYYWG | CRABRYTARB | YRRMVDTWYG |
|      | RTCTRVTRRM | | | |
|      | ACCATAGGTA | CATGGAATTG | ACAGTCATAT | AGAATTTKAA |
|      | TACCAGATAT | WWAMGWRRWC | GYTVYRATYV | RYYKBHAWRC |
|      | YAGAYBAYYK | | | |

FIGURE 4a (cont.)

1261 DVMRMRMWMA   RWAVMAWRMA   WRDARAGGGG   CCAATTCGCC
CTATAGTGAA TCGTGGTACA AANTTC

HBKYKYKWKT   YWTBKTWYKT   WYHTYTCCCC   GGTTAAGCGG
GATATCACTT AGCACCATGT TTNAAG

FIGURE 4a (cont.)

```
  1 MARERREIKR   IESAAARQVT   FSKRRRGLFK   KAEELSVLCD
    ADVALIVFSS

51 TGKLSQFASS   SMNEIIDKYS   THSKNLGKAD   QPSLDLNLEH
    SKYANLNDQL

101 AEASLRLRQM   RGEGLEGLXV   DELQQLEKNL   ETGLHRVLQT
    KDQQFLEQIN

151 ELQRKSSQLA   EENMQLRNQV   SQIPIAGKPV   VADTENVIAE
    DGQSSESVMT

201 ALHSGSSQDN  DDGSDVSLKL  GLPCSAWK
```

FIGURE 4b

```
tggcgmgggagaggcgcgagatcaagcggatagagagcgcggcggcgcgccaggtcaccttctccaagcgccgcaggggcctcttcaagaaggcc
gaggagctctccgtmctatgcgacgccgacgtcgcgctcatcgtcttctcgtccacagggaagctctcccagttcgcaagctccagtatgaatgagatcat
cgacaagtacagcacmcattctaagaacctggggaaagcagaccagccttctcttgacttgaayttagaacatagtaagtatgcaaatctgaacgatcag
cttgcggaagctagtctycgacttngacagatgagaggcgagggcttgaggggttgavtgttgatgaactccagcagttggagaagaaccttgaactg
gtctgcacaggggtgcttcagacgaaagatcaacaattcttggagcagatcaatgaattgcaacgaaagagctcacagctggcagaggagaacatgcaac
tgaggaaccaagtatcccagataccaatagctggcaagccagtagttgctgataccgaaaatgttattgctgaggatgggcagtcctctgaatctgtcatga
cggcgttgcactcgggaagcksacaggataacgatgatggttcagaygtatccctgaaattgggattacccctgcagtgcgtggaag
```

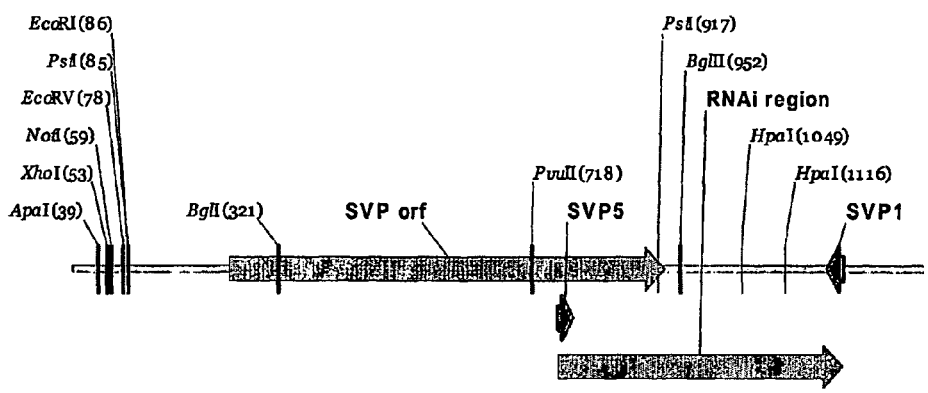

SVP orf
1329 bp

```
gataccaatagctggcaagccagtagttgctgataccgaaaatgttattgctgaggatgggcagtcctctgaatct
gtcatgacggcgttgcactcgggaagcksacaggataacgatgatggttcagaygtatccctgaaattgggatt
accctgcagtgcgtggaagtaactatataaaaycgtcrsttcagatctttatggaactgcccacrtcagtggagaa
gctcttgtgtaatcsacaaacgtaccygagctgcaataatcttgcrgctgaagcgagatcagttaacctgatttatc
atccttgtggctgcatgacgtgatgttmccgttyttacygtttactaggatgttaactaaactttagatcgatctgat
atccatctvatccccattermactattwgttcatagtawccatgtaccttaactgtcagtatatc
```

```
MARERRBIKR  IESAAARQVT  FSKRRRGLFK  KABELSVLCD  ADVALIVFSS
TGKLSQFASS  SMNBIIDKYS  THSKNLGKAD  QPSLDLNLEH  SKYANLNDQL
AEASLRLRQM  RGEGLEGLXV  DELQQLEKNL  ETGLHRVLQT  KDQQFLEQIN
ELQRKSSQLA  BENMQLRNQV  SQIPIAGKPV  VADTENVIAE  DGQSSESVMT
ALHSGSXQDN  DDGSDVSLKL  GLPCSAWK
```

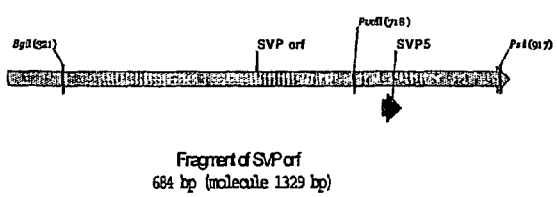

Fragment of SVP orf
684 bp (molecule 1329 bp)

FIGURE 4c

FLOWERING INHIBITION

The present invention relates to nucleic acid fragments encoding amino acid sequences for proteins involved in the control of flowering in plants, and the use thereof for the modification of flowering, particularly inhibiting flowering.

Genetic pathways that control flowering time in the model plant *Arabidopsis thaliana* have been studied recently, and progress in identification of genes that control key steps in these pathways has been made, see[1-4] for a review. It was found that increased expression of the FLOWERING LOCUS T (FT) gene leads to accelerated floral development, and almost complete loss of a normal photoperiodic response[5-7]. This flowering promoting action of FT is counteracted in part by the TERMINAL FLOWER (TFL) gene product, which acts as a repressor, but has significant sequence similarity to FT[8,9]. The FT family is comprised of 6 genes in *arabidopsis*, and of 9 genes in rice. With regard to this family, there is data to support validity of the *arabidopsis* model of the genetic control of flowering time when applied to other plant species. Rice heading date (flowering time) QTL mapping[10] and identification of the genes underlying natural variation revealed the same genetic pathway, at least for the photoperiodic control of flowering[11-13], despite the fact that rice has the short day photoperiod as opposed to the long day one of *arabidopsis*. Increased expression of the putative rice orthologue of FT called Hd3a seems to correlate with transition to flowering[14]. The LpTFL gene *Lolium perenne* described previously has been shown to function in *arabidopsis* in the expected way[15,16], so these genes appear to be attractive targets for attenuating photoperiodic signalling.

In addition to FT, which is believed to be at the final stage of the photoperiodic signal transduction chain, the GIGANTEA (GI) gene has been shown to affect flowering dramatically, and it is positioned early in the interface of the circadian clock and the photoperiod perception mechanisms[17-20]. The gene is present as a single copy in *arabidopsis* and in rice, and its manipulation in rice has similar consequences as in *arabidopsis*, further supporting validity of the *arabidopsis* model for at least the photoperiodic control[14], both in short day and in long day plants.

Another inductive pathway in *arabidopsis* combines autonomous cues and vernalization signalling. While the flowering locus C (FLC) MADS box gene appears to be a central integrator for much of this signalling in *arabidopsis*[21,22], no corresponding gene in the monocots has been reported to day that would match the FLC either by sequence homology or by the functional assay. In *arabidopsis*, additional MADS box genes apart from FLC has been implicated in both the autonomous and vernalization control, often found in pairs that seem to have opposite effects on the trait[23-28]. Orthologues of these genes and combinations thereof could perform the FLC function in monocots, including cereals and forage grasses.

While there are a great number of mutants that display a delay in flowering in *arabidopsis*, there is no single mutation that would lead to a complete loss of flowering. This perhaps reflects redundancy of the many genetic elements, and parallelism in signalling via different pathways. However, it was shown that combining mutations in the three major pathways that control flowering (autonomous, photoperiodic, and GA-dependent) leads to a complete loss of flowering in the absence of vernalization treatment[29].

Therefore, while nucleic acid sequences encoding some of the proteins involved in the control of flowering have been isolated for certain species of plants, there remains a need for materials useful in the modification of flowering in a wide range of plants, and for methods for their use.

Accordingly, there is a need for a system that enables flowering to be reduced or delayed. In particular, such a system would be useful in forage plants.

It is an object of the present invention to overcome, or at least alleviate, one or more of these needs in light of the prior art.

In one aspect, the present invention provides substantially purified or isolated nucleic acids encoding amino acid sequences of FLOWERING LOCUS T (FT) and TERMINAL FLOWER (TFL) proteins, and functionally active fragments and variants thereof, the presence of which inhibits flowering.

The present invention also provides substantially purified or isolated nucleic acid fragments encoding amino acid sequences for a class of proteins, which are related to FT and TFL, the presence of which inhibits flowering. Such polypeptides are referred to herein as FT-like and TFL-like respectively. The genes which encode these polypeptides are expressed in a similar manner to FT and TFL, respectively. The invention also encompasses functionally active fragments and variants of nucleic acids encoding such polypeptides.

As used herein the term FT-like relates to polypeptides that are produced in the plant in substantially the same organs and at substantially the same developmental stages as FT.

As used herein the term TFL-like relates to polypeptides that are produced in the plant in substantially the same organs and at substantially the same developmental stages as TFL.

In a further aspect, the present invention provides substantially purified or isolated nucleic acids encoding amino acid sequences of GIGANTEA (GI) and SHORT VEGETATIVE PHASE (SVP) proteins, and functionally active fragments and variants thereof.

The present invention also provides substantially purified or isolated nucleic acid fragments encoding amino acid sequences for a class of proteins, which are related to GI and SVP, and functionally active fragments and variants thereof. Such polypeptides are referred to herein as GI-like and SVP-like, respectively. The genes which encode these polypeptides are expressed in a similar manner to GI and SVP, respectively. The invention also encompasses functionally active fragments and variants of nucleic acids encoding such polypeptides.

As used herein the term GI-like relates to polypeptides that are produced in the plant in substantially the same organs and at substantially the same developmental stages as GI.

As used herein the term SVP-like relates to polypeptides that are produced in the plant in substantially the same organs and at substantially the same developmental stages as SVP.

The nucleic acid fragments are obtained from ryegrass (*Lolium*) or fescue (*Festuca*) species. These species may be of any suitable type, including Italian or annual ryegrass, perennial ryegrass, tall fescue, meadow fescue and red fescue. Preferably the species is a ryegrass, more preferably perennial ryegrass. (*L. perenne*).

Nucleic acids according to the invention may be full-length genes or part thereof, and are also referred to as "nucleic acid fragments" and "nucleotide sequences" on this specification.

The nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof.

The term "isolated" means that the material is removed from its original environment (e.g. the natural environment if it is naturally occurring). For example, a naturally occurring nucleic acid fragment or polypeptide present in a living plant is not isolated, but the same nucleic acid fragment or polypeptide separated from some or all of the coexisting materials in the natural system, is isolated. Such an isolated nucleic acid fragment could be part of a vector and/or such nucleic acid fragments could be part of a composition, and still be isolated in that such a vector or composition is not part of its natural environment.

By "functionally active" in respect of a nucleotide sequence is meant that the fragment or variant (such as an analogue, derivative or mutant) is capable of modifying flowering in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 30 nucleotides, more preferably at least 45 nucleotides, most preferably at least 60 nucleotides.

By "functionally active" in the context of a polypeptide is meant that the fragment or variant has one or more of the biological properties of the FT, FT-like, TFL, TFL-like, GI, GI-like, SVP or SVP-like proteins. Additions, deletions, substitutions and derivatizations of one or more of the amino acids are contemplated so long as the modifications do not result in loss of functional activity of the fragment or variant. Preferably the functionally active fragment or variant has at least approximately 60% identity to the relevant part of the above mentioned sequence, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

By "operatively linked" is meant that a regulatory element is capable of causing expression of said nucleic acid in a plant cell and said terminator is capable of terminating expression of said nucleic acid in a plant cell. Preferably, said regulatory element is upstream of said nucleic acid and said terminator is downstream of said nucleic acid.

By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

It will also be understood that the term "comprises" (or its grammatical variants) as used in this specification is equivalent to the term "includes" and should not be taken as excluding the presence of other elements or features.

Reference to any prior art in the specification is not, and should not be taken as, an acknowledgment or any form of suggestion that this prior art forms part of the common general knowledge in Australia or any other jurisdiction.

In a preferred embodiment of this aspect of the invention, the substantially purified or isolated nucleic acid fragment encoding a FT or TFL protein includes a nucleotide sequence selected from the group consisting of (a) sequences shown in FIG. 1 hereto (Sequence ID Nos: 1-5); (b) complements of the sequences recited in (a); (c) sequences antisense to the sequences recited in (a) and (b); (d) functionally active fragments and variants of the sequences recited in (a), (b) and (c); and (e) RNA sequences corresponding to the sequences recited in (a), (b), (c) and (d).

In a preferred embodiment of this aspect of the invention, the substantially purified or isolated nucleic acid fragment encoding a GI or SVP protein includes a nucleotide sequence selected from the group consisting of (a) sequences shown in FIGS. 3 and 4 hereto (Sequence ID Nos. 6-12); (b) complements of the sequences recited in (a); (c) sequences antisense to the sequences recited in (a) and (b); (d) functionally active fragments and variants of the sequences recited in (a), (b) and (c); and (e) RNA sequences corresponding to the sequences recited in (a), (b), (c) and (d).

The nucleic acid fragments of the present invention may be used to isolate cDNAs and genes encoding homologous proteins from the same or other plant species.

Additionally, genes encoding other flowering control proteins, either as cDNAs or genomic DNAs, may be isolated directly by using all or a portion of the nucleic acid fragments of the present invention as hybridisation probes to screen libraries from the desired plant employing the methodology known to those skilled in the art. Specific oligonucleotide probes based upon the nucleic acid sequences of the present invention can be designed and synthesized by methods known in the art. Moreover, the entire sequences can be used directly to synthesize DNA probes by methods known to the skilled artisan such as random primer DNA labelling, nick translation, or end-labelling techniques, or RNA probes using available in vitro transcription systems. In addition, specific primers can be designed and used to amplify a part or all of the sequences of the present invention. The resulting amplification products can be labelled directly during amplification reactions or labelled after amplification reactions, and used as probes to isolate full length cDNA or genomic fragments under conditions of appropriate stringency.

In addition, two short segments of the nucleic acid fragments of the present invention may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the nucleic acid fragments of the present invention, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, those skilled in the art can follow the RACE protocol[30] (the entire disclosure of which is incorporated herein by reference) to generate cDNAs by using PCR to amplify copies of the region between a single point in the transcript and the 3' or 5' end. Using commercially available 3' RACE and 5' RACE systems (BRL), specific 3' or 5' cDNA fragments can be isolated[31,32]. Products generated by the 3' and 5' RACE procedures can be combined to generate full-length cDNAs.

In a further aspect of the present invention there is provided a substantially purified or isolated polypeptide from a ryegrass. (*Lolium*) or fescue (*Festuca*) species, selected from the group consisting of FT, FT-like, TFL and TFL-like proteins, and functionally active fragments and variants thereof.

The ryegrass (*Lolium*) or fescue (*Festuca*) species may be of any suitable type, including Italian or annual ryegrass, perennial ryegrass, tall fescue, meadow fescue and red fescue. Preferably the species is a ryegrass, more preferably perennial ryegrass. (*L. perenne*).

In a preferred embodiment of this aspect of the invention, there is provided a substantially purified or isolated FT, FT-like, TFL or TFL-like polypeptide including an amino acid sequence selected from the group of sequences translated from nucleotide sequences shown in. FIG. 1 hereto (Sequence ID Nos. 1-5); and functionally active fragments and variants thereof.

In a further embodiment of this aspect of the invention, there is provided a polypeptide recombinantly produced from a nucleic acid according to the present invention. Techniques for recombinantly producing polypeptides are known to those skilled in the art.

In a further aspect of the present invention there is provided a substantially purified or isolated polypeptide from a ryegrass (*Lolium*) or fescue (*Festuca*) species, selected from the group consisting of GI, GI-like, SVP and SVP-like proteins, and functionally active fragments and variants thereof.

In a preferred embodiment of this aspect of the invention, there is provided a substantially purified or isolated GI, GI-like, SVP and SVP-like polypeptide including an amino acid sequence selected from the group consisting of (a) sequences translated from nucleotide sequences shown in FIGS. 3 and 4 hereto (Sequence ID Nos. 8, 10 and 11); (b) sequences shown in FIGS. 3 and 4 hereto (Sequence ID Nos. 9 and 12); and (c) functionally active fragments and variants of (a) and (b).

In a further embodiment of this aspect of the invention, there is provided a polypeptide recombinantly produced from a nucleic acid according to the present invention. Techniques for recombinantly producing polypeptides are known to those skilled in the art.

Availability of the nucleotide sequences of the present invention and deduced amino acid sequences facilitates immunological screening of cDNA expression libraries. Synthetic peptides representing portions of the instant amino acid sequences may be synthesized. These peptides can be used to immunise animals to produce polyclonal or monoclonal antibodies with specificity for peptides and/or proteins comprising the amino acid sequences. These antibodies can be then used to screen cDNA expression libraries to isolate full-length cDNA clones of interest.

A genotype is, the genetic constitution of an individual or group. Variations in genotype are essential in commercial breeding programs, in determining parentage, in diagnostics and fingerprinting, and the like. Genotypes can be readily described in terms of genetic markers. A genetic marker identifies a specific region or locus in the genome. The more genetic markers, the finer defined is the genotype. A genetic marker becomes particularly useful when it is allelic between organisms because it then may serve to unambiguously identify an individual. Furthermore, a genetic marker becomes particularly useful when it is based on nucleic acid sequence information that can unambiguously establish a genotype of an individual and when the function encoded by such nucleic acid is known and is associated with a specific trait. Such nucleic acids and/or nucleotide sequence information including single nucleotide polymorphisms (SNPs), variations in single nucleotides between allelic forms of such nucleotide sequence, can be used as perfect markers or candidate genes for the given trait.

In a further aspect of the present invention there is provided a method of isolating a nucleic acid of the present invention including a single nucleotide polymorphism (SNP), said method including sequencing nucleic acid fragments from a nucleic acid library.

The nucleic acid library may be of any suitable type and is preferably a cDNA library. The nucleic acid fragments may be isolated from recombinant plasmids or may be amplified, for example using polymerase chain reaction. The sequencing may be performed by techniques known to those skilled in the art.

In a further aspect of the present invention, there is provided use of nucleic acids of the present invention including SNP's, and/or nucleotide sequence information thereof, as molecular genetic markers.

In a further aspect of the present invention there is provided use of a nucleic acid according to the present invention, and/or nucleotide sequence information thereof, as a molecular genetic marker. More particularly, nucleic acids according to the present invention and/or nucleotide sequence information thereof may be used as a molecular genetic marker for quantitative trait loci (QTL) tagging, QTL mapping, DNA fingerprinting and in marker assisted selection, particularly in ryegrasses and fescues. Even more particularly, nucleic acids according to the present invention and/or nucleotide sequence information thereof may be used as molecular genetic markers in forage and turf grass improvement, e.g. tagging QTLs for herbage quality traits, dry matter digestibility, mechanical stress tolerance, disease resistance, insect pest resistance, plant stature, leaf and stem colour. Even more particularly, sequence information revealing SNPs in allelic variants of the nucleic acids of the present invention and/or nucleotide sequence information thereof may be used as molecular genetic markers for QTL tagging and mapping and in marker assisted selection, particularly in ryegrasses and fescues.

In a still further aspect of the present invention there is provided a construct including a nucleic acid according to the present invention. The construct may be a vector. In a preferred embodiment of this aspect of the invention, the vector may include a regulatory element such as a promoter, a nucleic acid according to the present invention and a terminator; said regulatory element, nucleic acid and terminator being operatively linked.

The vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, or integrative or viable in the plant cell.

The regulatory element and terminator may be of any suitable type and may be endogenous to the target plant cell or may be exogenous, provided that they are functional in the target plant cell.

In another embodiment, the construct or vector may include more than one nucleic acid. The nucleic acids within the same construct or vector may have identical or differing sequences. In one preferred embodiment, the construct or vector has at least two nucleic acids encoding proteins involved in the control of flowering.

In another preferred embodiment the construct or vector may include one or more FT or FT-like nucleic acids and one or more TFL or TFL-like nucleic acids according to the present invention, or functionally active fragments or variants thereof, in combination with other genes involved in the control of flowering timing. The genes involved in the control of flowering timing may be selected from a group consisting of GIGANTEA (GI), G-like, SVP and SVP-like, and fragments and variants thereof.

Preferably one of the regulatory element is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (e.g. monocotyledon or dicotyledon). Particularly suitable constitutive promoters include the Cauliflower Mosaic Virus 35S (CaMV 35S) promoter, the maize Ubiquitin promoter, and the rice Actin promoter.

A variety of terminators which may be employed in the vectors of the present invention are also well known to those skilled in the art. It may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the regulatory element, the nucleic acid of the present invention and the terminator, may include further elements necessary for expression of the nucleic acid, in different combinations, for example vector backbone, origin of replication (ori), multiple cloning sites, spacer sequences, enhancers, introns (such as the maize Ubiquitin. Ubi intron), antibiotic resistance genes and other selectable marker genes (such as the neomycin phosphotransferase (npt2) gene, the hygromycin phosphotransferase (hph) gene, the phosphinothricin acetyltransferase (bar or pat) gene), and reporter genes (such as beta-glucuronidase (GUS) gene (gusA). The vector may also contain a ribosome binding site for translation initiation. The vector may also include appropriate sequences for amplifying expression.

As an alternative to use of a selectable marker gene to provide a phenotypic trait for selection of transformed host cells, the presence of the construct or vector in transformed cells may be determined by other techniques well known in the art, such as PCR (polymerase chain reaction), Southern blot hybridisation analysis, histochemical GUS assays, northern and Western blot hybridisation analyses.

Those skilled in the art will appreciate that the various components of the construct or vector are operatively linked, so as to result in expression of said nucleic acid. Techniques for operatively linking the components of the construct or vector of the present invention are well known to those skilled in the art. Such techniques include the use of linkers, such as synthetic linkers, for example including one or more restriction enzyme sites.

The constructs and vectors of the present invention may be incorporated into a variety of plants, including monocotyledons (such as grasses from the genera *Lolium, Festuca, Paspalum, Pennisetum, Panicum* and other forage and turf-grasses, corn, rice, sugarcane, oat, wheat and barley, dicotyledons, such as *arabidopsis*, tobacco, soybean, canola, cotton, potato, chickpea, medics, white clover, red clover, subterranean clover, alfalfa, eucalyptus, poplar, hybrid aspen, and gymnosperms (pine tree). In a preferred embodiment, the constructs and vectors are used to transform monocotyledons, preferably grass species such as ryegrasses (*Lolium* species) and fescues (*Festuca* species), even more preferably a ryegrass, most preferably perennial ryegrass, including forage- and turf-type cultivars.

Techniques for incorporating the constructs and vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the constructs and vectors of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a construct or vector of the present invention.

The plant cell, plant, plant seed or other plant part may be from any suitable species, including monocotyledons, dicotyledons and gymnosperms. In a preferred embodiment the plant cell, plant, plant seed or other plant part is from a monocotyledon, preferably a grass species, more preferably a ryegrass (*Lolium* species) or fescue (*Festuca* species), even more preferably a ryegrass, most preferably perennial ryegrass, including both forage- and turf-type cultivars.

The present invention also provides a plant, plant seed or other plant part derived from a plant cell of the present invention. The present invention also provides a plant, plant seed or other plant part derived from a plant of the present invention.

In a further aspect of the present invention there is provided a method of modifying flowering in a plant, said method including introducing into said plant an effective amount of a nucleic acid, construct and/or vector according to the present invention. Preferably the method includes inhibiting flowering in said plant.

In a preferred embodiment more than one regulatory gene is manipulated, to inactivate multiple redundant and parallel genetic pathways that normally promote flowering in response to internal and external cues. The manipulated genes can be the FT/TFL family members, including both promoters and repressors; orthologs of the Gigantea (GI) gene, to disrupt the circadian clock, and therefore to interfere with the photoperiodic response; and the AGL24/SVP MADS box transcription factors, to interfere with response to autonomous and vernalization signals.

To inactivate a gene, either the RNA interference in transgenic plants can be used, or naturally or artificially induced hypomorphic alleles could be identified and bred into a production cultivar.

Using the methods and materials of the present invention, flowering may be accelerated or delayed. It may be accelerated, for example, by incorporating additional copies of a sense nucleic acid of the present invention. It may be delayed, for example, by incorporating an antisense nucleic acid or dsRNA or small interfering RNA (siRNA) derived from the nucleotide sequences of the present invention. In addition, the number of copies of genes encoding for different proteins involved in the timing of flowering may be simultaneously manipulated to modify flowering.

In a further aspect of the present invention there is provided a preparation for transforming a plant comprising at least one nucleic acid according to the present invention. The preparation may contain vectors or other constructs to facilitate administration to and/or transformation of the plant with the nucleic acid.

The principle of elimination of flowering combined attenuation of expression of genes that control different genetic pathways that is described here can be applied to ryegrass to better control pasture production cycle, and to improve persistence by allowing a more controlled heading. The technology to eliminate flowering can be used in combination with system for accelerating or initiating flowering to achieve complete artificial control over vegetative to floral transition that will be independent of weather and growth conditions. Consequently, its application should not be limited to just forage grasses, and such system can be applied to any agricultural crop to facilitate more controlled production, and reduce dependence of yields on weather.

Additionally, ability to eliminate natural flowering may be a prerequisite for the release of transgenic plants into the field due to regulatory requirements.

The present invention will now be more fully described with reference to the accompanying Examples and drawings. It should be understood, however, that the description following is illustrative only and should not be taken in any way as a restriction on the generality of the invention described above.

In the Figures:

FIG. 1 shows the sequences of RgFT1 (SEQ ID No. 2), RgFT2 (SEQ ID No. 1), RgMFT (SEQ ID No. 3), RgTFL1 (SEQ ID No. 5) and RgTFL2 (SEQ ID No. 4).

FIG. 3 shows the sequence of the putative ryegrass ortholog of the GI gene (SEQ ID Nos. 6 and 7).

FIG. 4*a* shows the complete cDNA sequence of the RgSVP gene (SEQ ID No. 8).

FIG. 4*b* shows a translation of the RgSVP coding region (SEQ ID No. 9).

FIG. 4*c* shows the gene structure of ryegrass SVP (SEQ ID Nos. 10-12).

Figure 2:
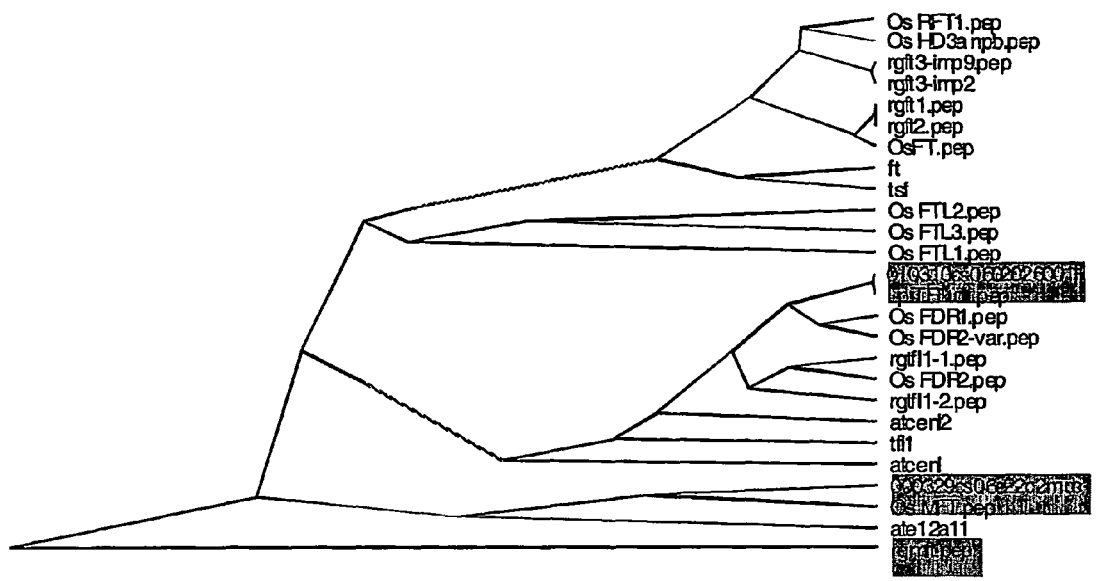
FIG. 2 shows the alignment of translated protein sequences for RgFT2, RgFT1, RgTFL1 and RgTFL2 in comparison to the sequences from other species.
Figure 5:
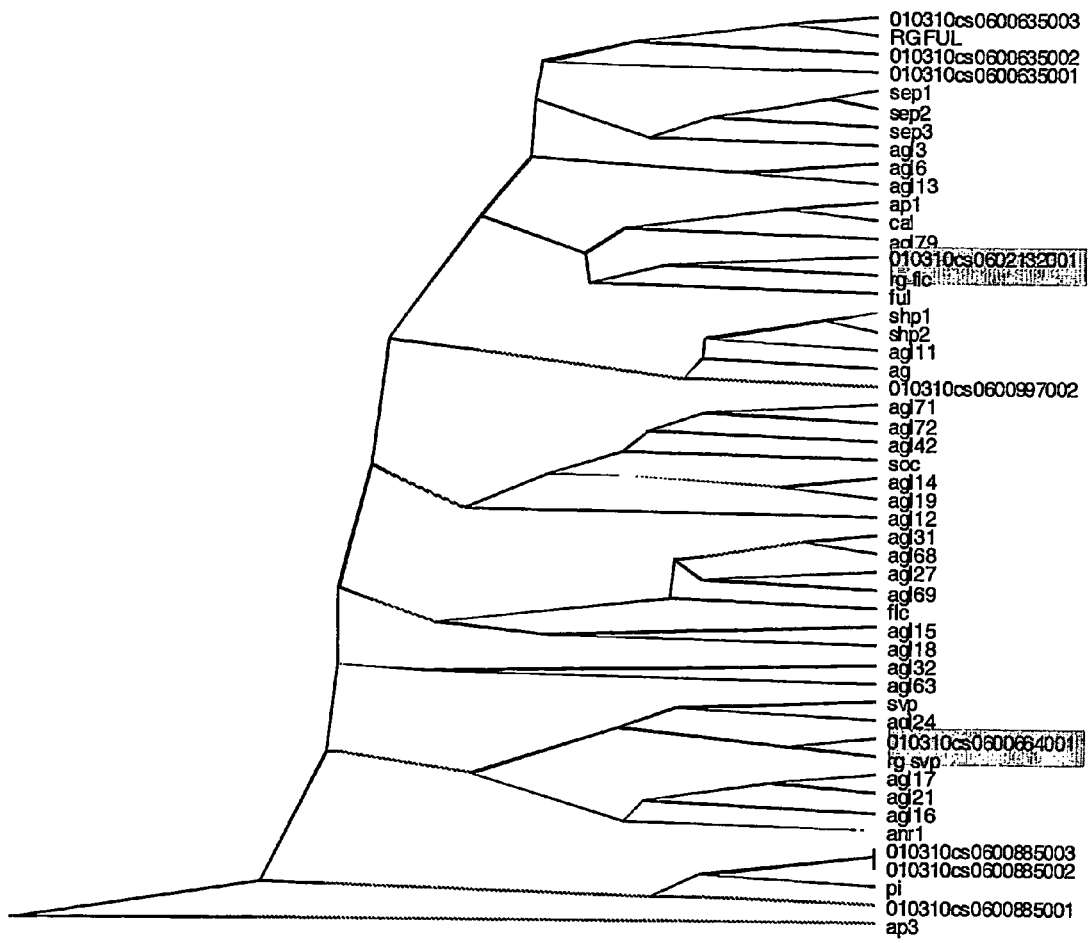

FIG. 5 shows the alignment of RgSVP predicted protein sequence with SVP proteins for other species.

Figure 6:
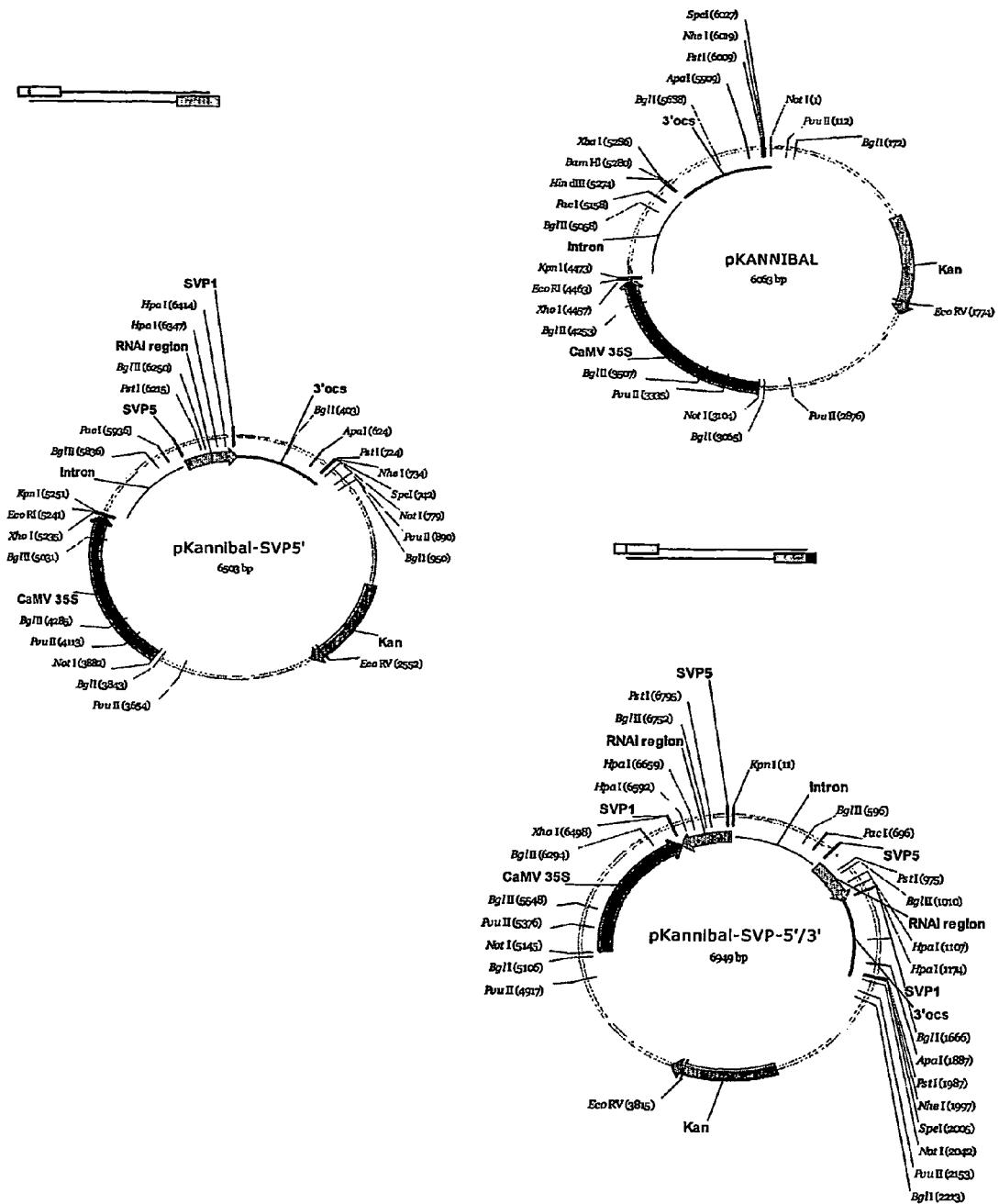

FIG. 6 shows the RNA interference construct to inactivate the RgSVP gene.

Figure 7:
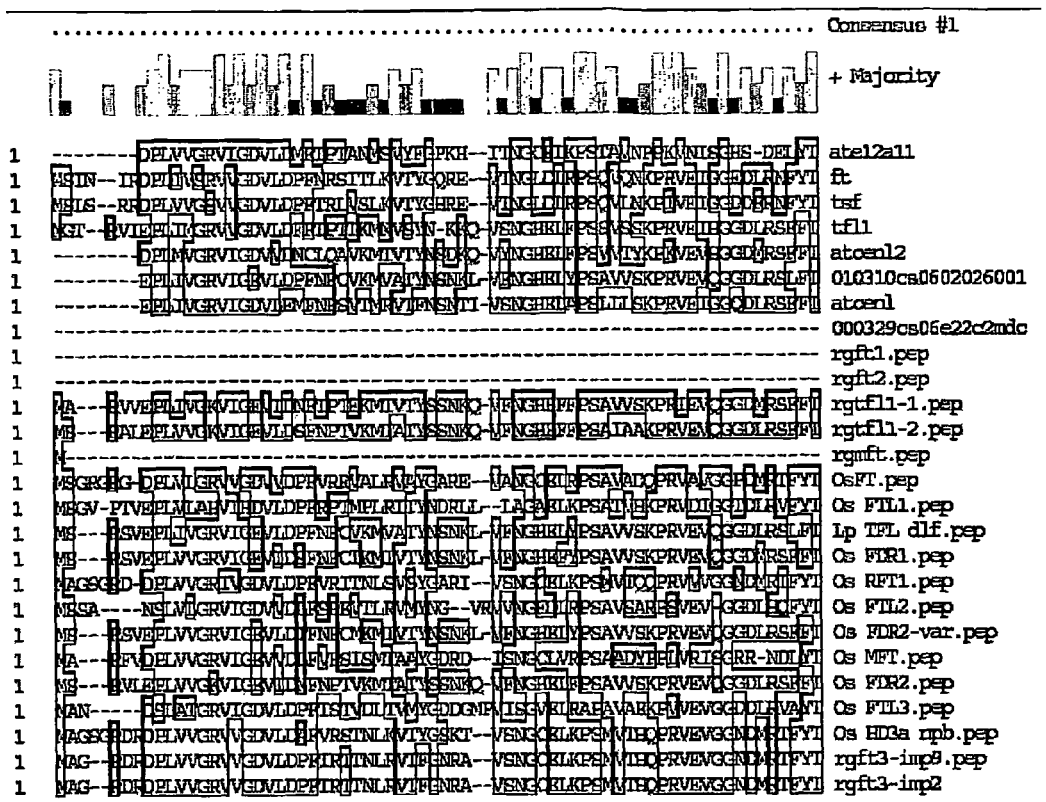
Figure 7:
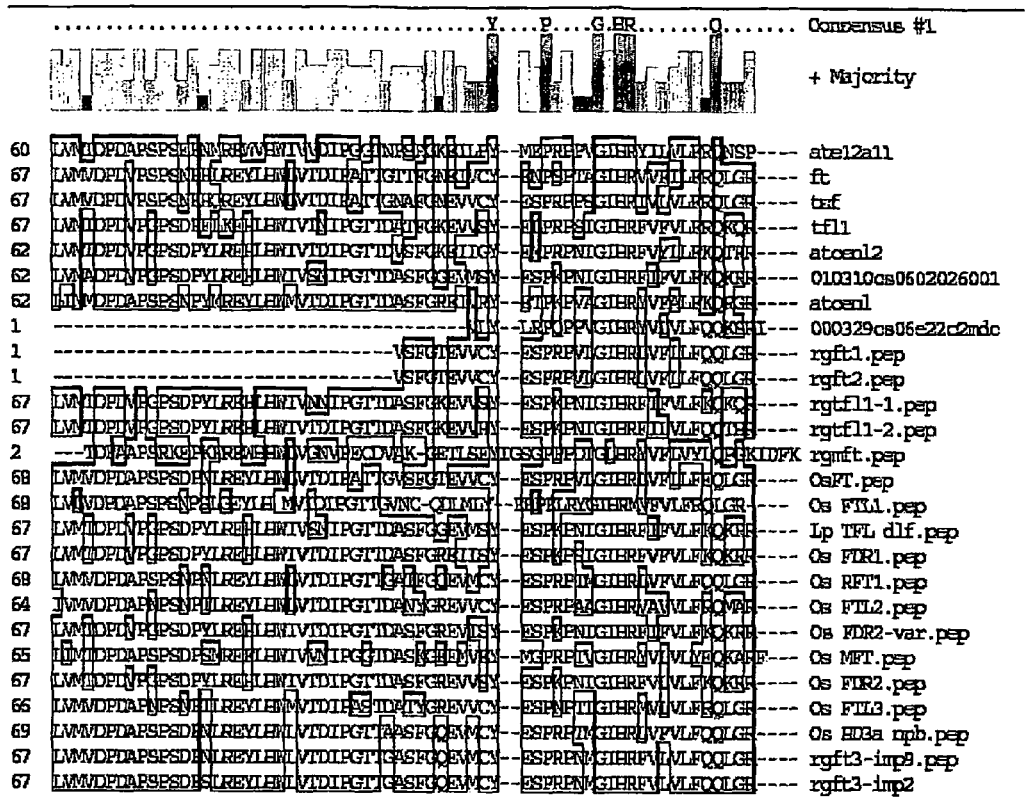
Figure 7:
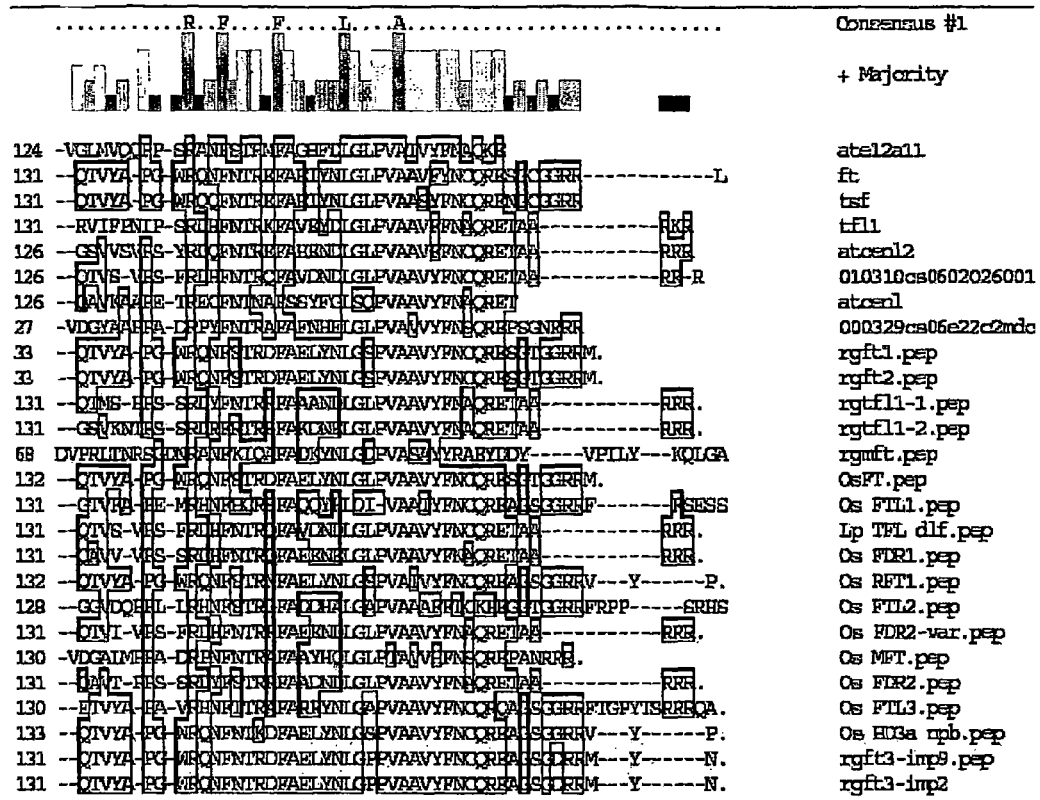

FIG. 7 shows the alignment of protein translations of the ryegrass members of the FT/TFC family with those from other plant species (SEQ ID Nos. 13-38).

Figure 8:
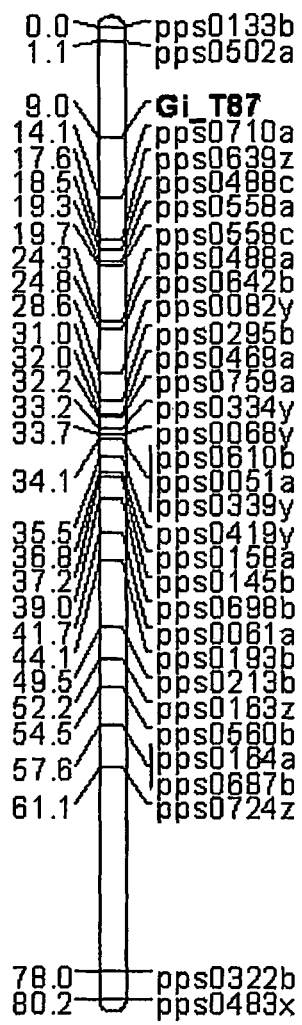

FIG. 8 is a genetic linkage map of perennial ryegrass linkage group LG3, showing the position of the Gigantea gene in the ryegrass map of the linkage group 3. Marker locus names are indicated on the right side of the bar, with centimorgan (cM) distances on the left. The RgGI SNP marker is indicated in bold. The remaining loci, prefixed 'pps', are EST-SSR loci.

Figure 9:
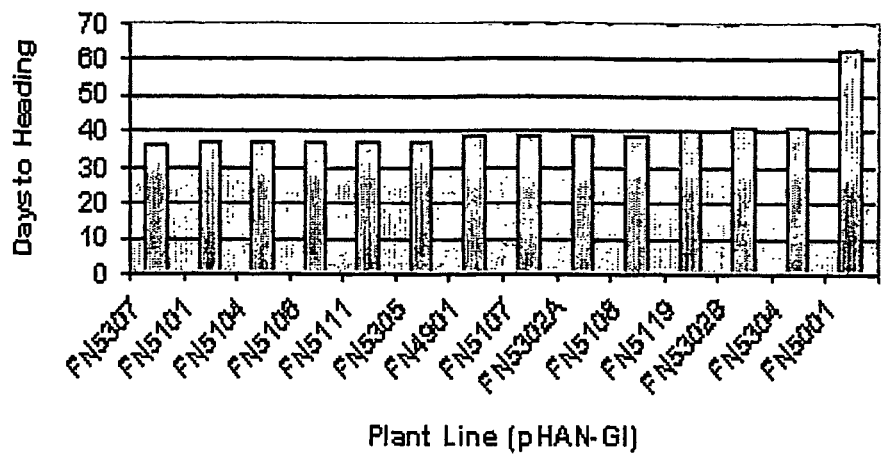

FIG. 9 shows heading dates for LpG/RNAi transgenics. The line FN5001 flowered substantially later then the others.

Figure 10:
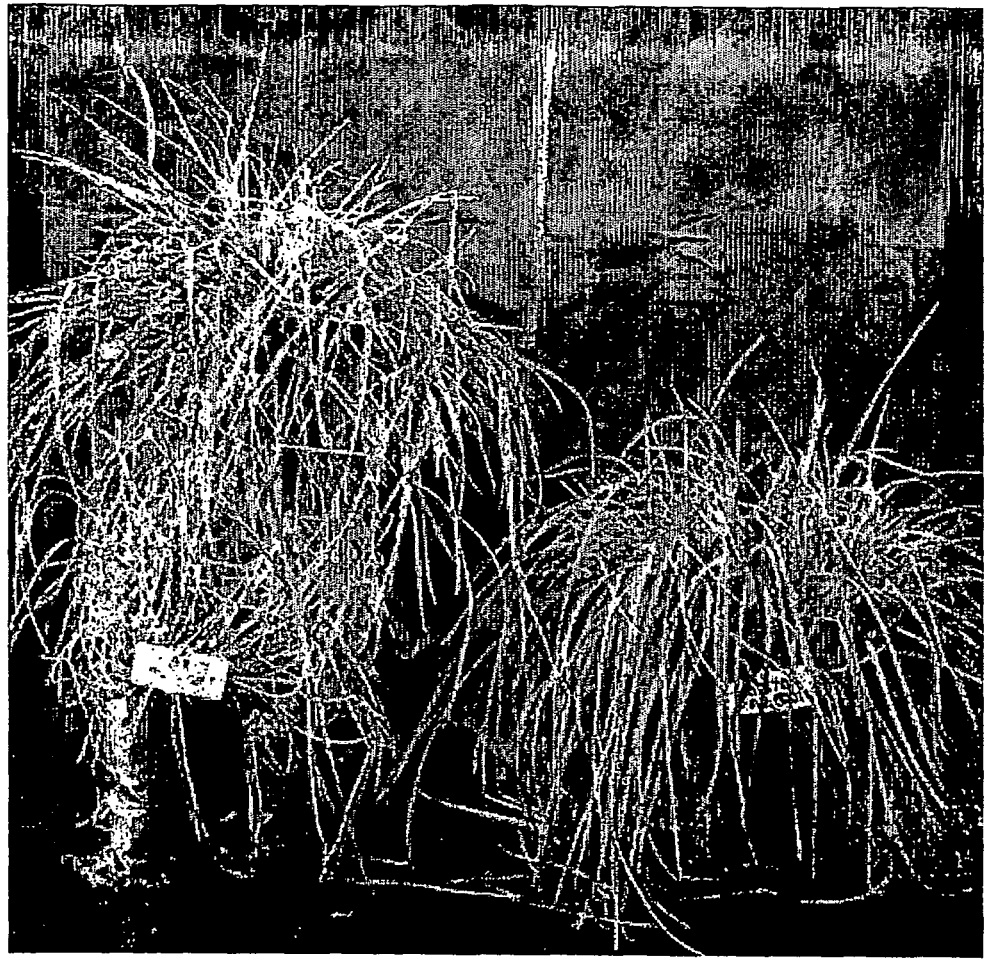

FIG. 10 shows delayed flowering phenotypes of a GI-RNAi ryegrass transformant FN5001 (right).

Figure 11:
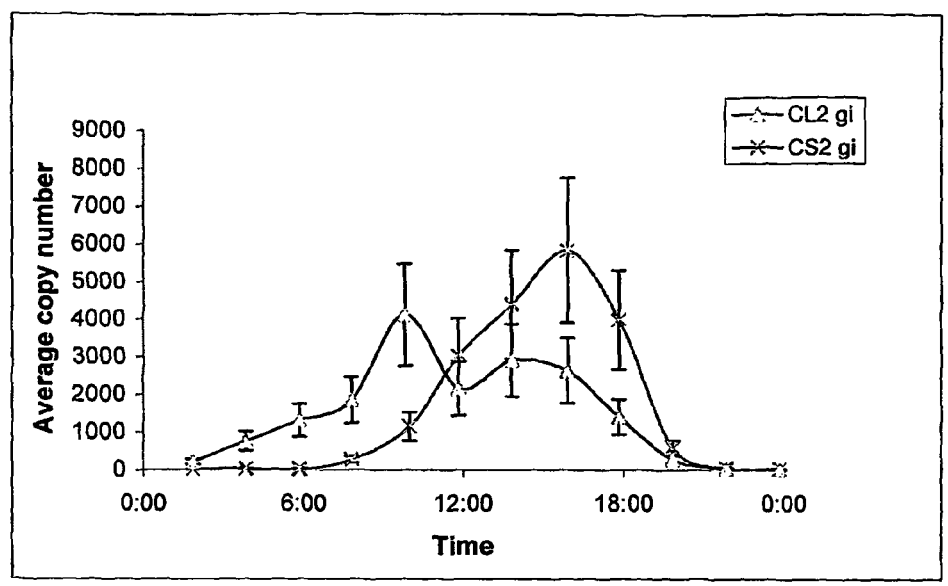

FIG. 11 Circadian expression of the RgGI gene as measured by quantitative RT-PCR CL2 represents samples collected in long day conditions, CS2 samples were harvested in short days.

EXAMPLES

1. FT/TFL

Gene Isolation

Partial sequences of the other two FT-like genes of ryegrass, called RgFT1 and 2, and 2 members of the TFL-like subfamily RgTFL1 and 2 were isolated. These share significant sequence similarity with FT, but perform the opposite function of floral repression in *arabidopsis*[8,9,33] rather than accelerating flowering cDNAs for these genes were isolated using degenerate primers design to amplify conserved regions of the family. Complete cDNA sequences, where available, were obtained by 3' and 5'RACE. Sequences of these additional members of the ryegrass family are shown in FIG. 1.

For the purposes of inactivation of normal transition, these genes can be manipulated as follows:

RgFT1, 2 and 3 are inactivated via RNAi in transgenics, TILLING, or identification and selective breeding to fix hypomorphic natural alleles.

RgTFL1, 2 and LpTFL are constitutively overexpressed, using appropriate transgenic constructs.

Polymorphism Analysis

We have identified the following polymorphisms within the ryegrass FT/TFL family of genes, which can be used in mapping and allele association studies for identification of hypomorphic alleles:

| gene | pos | translation | comment |
|---|---|---|---|
| Rgft1 | 190 | silent | |
| Rgft1 | 325 | polyA | 50 bp extra |
| Rgft1 | 99 | Q-R | observed variant, more common in tfls |
| Rgft1 | 325 | polyA | 90 bp extra |
| Rgft1 | 156 | L-P | |
| Rgft1 | 190 | silent | |
| Rgft1 | 325 | polyA | 32 bp extra |
| Rgft1 | 133 | silent | |
| Rgft1 | — | wt | wt sample |
| Rgft1 | 270 | 3'utr | |
| Rgft2 | 337 | 3'utr | |
| Rgft2 | 356 | polyA | 21 bp extra |
| Rgft2 | 356 | polyA | 28 bp extra |
| Rgft2 | 106 | silent | the same as the one that defines entry clones as rgft1 |
| Rgft2 | 184 | silent | |
| Rgft2 | — | wt | wt sample |
| Rgft2 | 283 | 3'utr | |
| Rgft2 | 356 | polyA | 19 bp extra |
| rgtfl1-1 | | | |
| rgtfl1-1 | 53 | 5' utr | |
| rgtfl1-1 | 160 | silent | |
| rgtfl1-1 | 395 | Trp->Arg | |
| rgtfl1-1 | 235 | silent | |
| rgtfl1-1 | 250 | silent | |
| rgtfl1-1 | 255 | silent | |
| rgtfl1-1 | 259 | silent | |
| rgtfl1-1 | 268 | silent | and some other silent ones not catalogued |
| rgtfl1-1 | 275 | Val->Ile | |
| rgtfl1-1 | 279 | Val-Ala | |
| rgtfl1-1 | 281 | Ser->Ala | |
| rgtfl1-1 | 293 | Ile->Val | |
| rgtfl1-1 | 314 | met->leu | |
| rgtfl1-1 | 405 | Asn->Thr | |
| rgtfl1-1 | 407 | Asn->Asp | |
| rgtfl1-2 | 12 | 5' utr | |
| rgtfl1-2 | 280 | Agr->Ile | |
| rgtfl1-2 | | | |
| rgtfl1-2 | 247 | Lys->Arg | |

2. Gigantea

Gene Isolation

Partial cDNA sequence of the putative ryegrass orthologue was identified in the cDNA library. Complete cDNA sequence was obtained using 5'-RACE.

The cDNA sequence and corresponding translation are shown in FIG. 3.

Sequence Analysis shows that the cDNA sequence of the putative ryegrass GI gene has been isolated, based on comparison with GI-like genes from other grasses. The sequence contains uninterrupted open reading frame representing the full-size ryegrass GI protein.

Polymorphism Analysis

By analysing diverse population of plants within a cultivar, and by comparison of the cultivars, we have identified the following genetic variation within the genomic sequence:

| trace name | wt | mut | pos | translation | comment |
|---|---|---|---|---|---|
| h6 | c | t | 209 | silent | |
| b2 | c/g het | c | 477 | silent | |
| e2 | c/g het | c | 477 | silent | in some others |
| est | c/g het | c | 477 | silent | |
| g6 | c/g het | c | 477 | silent | |
| a2 | T | a/t het | 607 | intron | |
| b4 | T | a/t het | 607 | intron | |
| d4 | T | a/t het | 607 | intron | |
| d6 | T | a/t het | 607 | intron | |
| e2 | T | a/t het | 607 | intron | |
| e4 | T | a/t het | 607 | intron | |
| f2 | T | a/t het | 607 | intron | |
| f4 | T | a/t het | 607 | intron | |
| multi | t | g | 637 | intron | both types and |
| multi | a | g | 644 | intron | both types and |
| b4 | t | t/c | 689 | intron | |
| b4 | t | t/c | 699 | intron | |
| a2 | ttaat | wt/agaca | 589–593 | intron | |
| b4 | ttaat | wt/agaca | 589–593 | intron | |
| d4 | ttaat | wt/agaca | 589–593 | intron | |
| d6 | ttaat | wt/agaca | 589–593 | intron | |
| e4 | ttaat | wt/agaca | 589–593 | intron | |
| f2 | ttaat | wt/agaca | 589–593 | intron | |
| f4 | ttaat | wt/agaca | 589–593 | intron | |

These variants are used to create markers, and to use in allele association studies.

Additionally, we have identified the following sequence polymorphisms between the parental lines of the mapping population:

| name | before | after | A8830/1030 | A10622/2 | pos | oligo |
|---|---|---|---|---|---|---|
| T87 | TGATGCATGTCATGAA GGCAATGAAG (SEQ ID No. 39) | CAATGTCTGTTCCC (SEQ ID No. 40) | C | Y | 87 | GIK17 |
| A125 | CGTGAGGAAATGAACA ACAGA (SEQ ID No. 41) | ACAAAGCAAAAAAT (SEQ ID No. 41) | T | W | 125 | GIK17 |

These polymorphisms were used to establish the map position of the ryegrass Gigantea gene as follows:

Methods:

Plant Material and DNA Isolation

The perennial ryegrass population used for the genetic mapping of the rgFT3 SNP (single nucleotide polymorphism) marker and SSR (simple sequence repeat) markers was an $F_1$ progeny set derived from a pair cross between the heterozygous parental genotypes A8830/1030 (from the cultivar 'Grasslands Samson') and A10622/2 (from the cultivar 'Grasslands Impact'). Ninety-four individual progeny from the population were used for genetic linkage analysis. Genomic DNA was extracted by the 1×CTAB method of Fulton et al. (1995).

EST-SSR and SNP Analysis

Genotypic data for 94 mapping population progeny was generated using 157 EST-SSRs and the RgGI SNP markers T87 and A125. EST-SSR PCR was conducted using the three primer protocol described by Schuelke (2000). An 8 μL reaction volume was used, containing 10 ng of genomic DNA, 2.5 mM magnesium chloride, 1×PCR buffer (Invitrogen, Carlsbad, Calif., USA), 0.05 mM of each dNTP, 0.0375 μM forward primer, 0.15 μM reverse primer, 0.15 μM of fluorescent-labelled M13 primer and 0.3 U of Platinum Taq DNA polymerase (Invitrogen). Fluorophores used were 6-FAM™, NED™, VIC™ and PET™ (Applied Biosystems, Foster City, Calif., USA). EST-SSR primers were synthesised and supplied by either Invitrogen or Integrated DNA Technologies (Coralville, Iowa, USA). PCR reactions were run in iCyclers (BioRad, Hercules, Calif., USA), employing the following profile: (1) 94° C. for 4:00 minutes, (2) 30 cycles of: 94° C. for 30 seconds, 55° C. for 30 seconds and 72° C. for 30 seconds, (3) 8 cycles of: 94° C. for 30 seconds, 53° C. for 30 seconds and 72° C. for 30 seconds, (4) 72° C. for 30 minutes.

PCR products were analysed on an ABI 3100 Genetic Analyser using a 22 cm capillary array with POP-7™ polymer (Applied Biosystems). Electropherograms were analysed using ABI Prism GeneScan (v 3.7, Applied Biosystems), and genotype data was scored using ABI Prism Genotyper (v 3.7, Applied Biosystems). The allelic status of the RgGI SNPs was determined by direct sequencing of amplification products produced with oligonucleotides

```
                                      (SEQ ID No. 43)
     GIK16      5'CATGAAATGTGCAGAACAGG3'
     and (SEQ ID No. 44)
     GIK17      5'TGGTTGACTCTCCACATCTTC3'.
```

Genetic Linkage Analysis

The A8830/1030×A10622 population was analysed as a two-way pseudo-testcross (Grattapaglia and Sederoff 1994). Genetic linkage analysis was conducted using the CP module of JoinMap® 3.0 software (www.kyazma.nl). Map distances in centimorgans (cM) were calculated using the Kosambi mapping function (Kosambi 1944). Genetic linkage maps were first established separately for A8830/1030 and A10622 using segregation data from EST-SSR and SNP markers that could be derived as dominant features. Polymorphic loci detected by the same. EST-SSR primer pair at similar locations on the maps of both parents were used to identify and align homologous linkage groups in the two parental maps, and to check for consistency of recombination frequency between the parental genotypes. Parental datasets were then combined and a consensus genetic linkage map was constructed, using a maximum recombination frequency of 0.4 and minimum LOD threshold of 2.0.

Results

Genetic linkage analysis enabled the location of 126 EST-SSR loci and the RgGI SNP on a consensus map covering 354 cM across seven linkage groups (LG1-LG7). The RgGI SNP mapped to a location at position 9 cM on LG3 (FIG. 8).

We have identified partial syntheny between the ryegrass LG3 and the rice chromosome 1 around the GI gene, as shown in the following table:

| rg map position | marker | rice BLAST hit acc no. | assigned to rice csome | BAC/PAC | Contig position on csome |
|---|---|---|---|---|---|
| 0 cM | pps0133b | AP003215 | 1 | OSJNBa0089K24 | 3724261bp–3878397bp |
| 1.1 cM | pps0502a | AC084763 | 10 | OSJNBa0027P10 | |
| 9.0 cM | gi_T87 | OsGI | 1 | AP003047_70329_141983 | 4326527bp–4333377bp |
| 14.1 cM | pps0710a | no hits | | | |
| 17.6 cM | pps0639z | AP002903 | 1 | P0509B06 | 4031060bp–4135574bp |
| 18.5 cM | pps0488c | AP002835 | 1 | P0417G05 | 6715722bp–6863524bp |
| 19.3 cM | pps0558a | AC091749 | 10 | OSJNBb0008A05 | |
| 24.3 cM | pps0488a | AP002835 | 1 | P0417G05 | 6715722bp–6863524bp |
| 24.8 cM | pps0642b | AP002481 | 1 | P0702F03 | 7336755bp–7477865bp |

Strong sequence similarity, and sythenic position of the ryegrass gene on the map support our claim that the ryegrass GI gene we identified functions in controlling photoperiodic flowering in ryegrass, and can be used to manipulate flowering behaviour of the plant.

Transgenic Plants

We have generated transgenic ryegrass plants in which expression of the GI gene is reduced by RNA interference, using the 3' end part of the cDNA sequence shown above. Of >20 independent transgenic plants obtained using this construct, one displayed significant delay in flowering compared to the others and to the non-transformed control, as shown in FIGS. 9 and 10.

(a) Expression Analysis of the RgGI Gene

Methods:

Ryegrass plants were grown outside and subjected to cold over the winter to achieve natural vernalization. They were then transferred to a glass house, and grown either in natural short day (SD) conditions (<11 hrs daylight), or with supplementary light to create artificial long day (LD) conditions (18 hr day). End of day in both conditions was at ~18:00. Plant samples were harvested as entire above-ground tillers 10 days after the long day treatment started, samples were taken every 2 hrs for 24 hours from both LD and SD treated plants.

Total RNA was extracted from samples using the Trizol protocol as follows:

Extraction of RNA from 1 g (nett) of *L. perenne* plant tissue using the Trizol® Reagent (Invitrogen)

Plant Tissue Pre-Homogenisation Treatment

Remove relevant bags of plant tissue from −80° C. freezer. Keep frozen in liquid $N_2$ or on dry ice until ready for treatment. Prechill coffee grinder by processing two dry ice pellets (7 g pellets).

NB: In between samples, wipe out the coffee grinder with 75% ethanol soaked kim wipes and repeat prechill step Weigh bag of tissue (approx 7-10 g). Empty contents into coffee grinder and blend until tissue is the consistency of salt granules (no larger). Pour coarsely ground tissue into a fresh prechilled bag and keep frozen until required for next stage. Reweigh just before taking sample for fine grinding (allowing for difference in bag weight).

Homogenisation

Remove 1.1-1.2 g of coarsely ground tissue (taking into account the increase of weight due to dry ice contribution) and ⊖ homogenise further in a prechilled mortar containing liquid $N_2$ until consistency of icing sugar. Add powder to 10 ml of Trizol® in mortar (room temperature) and homogenise further as quickly as possible. Pour soup into 14 ml disposable falcon tube. ⊖ Incubate samples at least 5 min at RT with gentle inversion.

Phase Separation

Add 2 ml chloroform per sample. Cap and mix vigorously 15 s by hand. Incubate RT 2-3 min. Spin in swinging bucket rotor at 3200×g for 30 min⊖ . Remove 4 ml to fresh tube (with modified cap*). There will be ~1 ml aqueous phase left, purposely done to reduce/avoid DNA contamination.

RNA Precipitation

Add 5 ml Isopropanol⊖ . Mix by inversion ~6 times. Incubate for 10 min at RT. Centrifuge at ≤2,000×g for 10 mins. Decant and discard supernatant.

RNA Wash

Add 10 ml 75% ethanol. Vortex and mix by inversion to wash lid. ⊖ Centrifuge ≤7,500×g, 5 mins, 4° C. Decant and discard supernatant. To reduce drying time, centrifuge again to collect excess wash solution to bottom of the tube at ≤7,500×g, 2 mins, 4° C. Remove excess liquid with RNAse-free pipette tip and airdry pellet approx 10-15 min.

RNA Resuspension

Add 0.8 ml of DEPC treated water. Gently resuspend pellet with pipette tip. Transfer liquid to eppendorf tube. An incubation at 55 C for 10 min. may be required if resuspension difficult.

RNA Storage

Store samples labelled well at −80° C. with bulk sample~700 ul and a 80 ul working aliquot.

Total RNA was converted to cDNA using standard protocols using 1-5 ug of RNA as measured by OD260.

Quantitative RT-PCR was performed in the BioRad iCycler instrument using standard protocols and SyberGreen as reporting dye Actin gene levels were assayed using oligonucleotides GTF037 5'GCTGTTTTCCCTAGCATTGTTGG3' (SEQ ID No. 45) and GTF038 5'ATAAGAGAATCCGTGAGATC-CCG3' (SEQ ID No. 46), and served as standards to normalize measurements of other genes.

RgGI mRNA levels were measured using oligonucleotides GIK16 and GIK17 described in the mapping example.

To create a copy number calibration curve for individual genes, standards were made up from corresponding. PCR products, measuring their concentration using gel serial dilution methods and spectrophotometry. Standard copy numbers were varied from 1 to 10^8 with 10× increments.

Amplifications were performed in triplicates, error rates were estimated by adding the average variance between triplicate samples, and average error of the standard curve fit of the standards of both the gene of interest and of the actin standard.

Results

The mRNA levels of the RgGI gene change significantly over the 24-hour cycle. The periodicity of expression suggests that the ryegrass gene, like its *arabidopsis* orthologue, is under the control of the circadian clock. The expression levels do not change significantly in photo inductive conditions, however, there may be a phase shift in long days to earlier increase, coincident with light exposure. Such circadian regulation of expression, as well as phase shift in long days, strongly support the role of the RgGI gene in mediating and controlling the photoperiodic floral response of ryegrass, as postulated in the external coincidence hypothesis for *arabidopsis*

3. RgSVP

Gene Isolation

The gene was identified in the EST collection, and the EST clone was completely sequenced. Diagram of the gene structure is shown in FIG. 4.

Sequence Analysis

Alignment of the RgSVP predicted protein translation has shown that it clusters with the *arabidopsis* SVP and AGL24 genes of *arabidopsis*, as shown in FIG. 5.

While SVP seems to be a repressor of floral development,[26,34] acting largely in the autonomous pathway, AGL24 seems to be involved in some promotive vernalization signalling that bypasses the FLC[23,35], providing an attractive target for inactivation of vernalization pathway.

The constructs for RNA interference to inactivate the RgSVP gene were created as shown in the FIG. 6.

Other RNAi-type constructs described here for FT/TFL and GI genes involved similar vector system and experimental approach.

Polymorphism Analysis

The following SNPs were identified upon sequencing cDNA and genomic clones derived from the genetically diverse stocks:

100 mm Petri plates containing LP5 medium*
100 mm Petri plates containing LP3-OS medium
100 mm Petri plates containing LP3 medium
100 mm Petri plates containing LP3 medium + 200 mg/L Hygromycin (Hm)
100 mm Petri plates containing MSK medium + 200 mg/L Hm
250 ml culture vessels containing MSO medium + 200 mg/L
Hygromycin stock solution (50 mg/ml in PDS, sterile)

Procedure

1) Harvest and surface sterilise floral tillers of *Lolium perenne* in 5% available chlorine Na-hypochlorite for 15 minutes using a Mason jar (or equivalent) under constant agitation.
2) Rinse tillers with autoclaved ddH$_2$O.
3) Aseptically dissect floral meristems.
4) Culture meristems on callus induction medium LP5 (16-20 explants per plate) and incubate in the dark for four to six weeks.
5) On the day of transformation transfer embryogenic callus material to high osmotic medium LP3-OS. Arrange approximately 4 cm$^2$ of calli in the centre of the Petri dish.
6) Incubate calli for 4-6 hours at room temperature.
7) Prepare particles and perform biolistic transformation following the protocol: "Biolistic Transformation of *Lolium perenne* with the Bio-Rad Particle Delivery System (PDS)". Plasmids are co-transformed. One plasmid (pAcH1) contains the hygromycin phosphotransferase gene conferring resistance to the antibiotic hygromycin expressed from the rice actin promoter and the second plasmid contains the genetic construct of interest for transformation. Plasmids are mixed in a one to one ratio at 1 μg/μL and simultaneously coated onto the microcarriers.

| allele | wt | mut | seq before | seq after | pos cDNA | translation | wt aa | conservation |
|---|---|---|---|---|---|---|---|---|
| SVP1 | T | G | CGCCATCGCCGCCTCCGA | TCTCGCGCCTCTCCC | 7 | G | W | high |
| SVP2 | G | T | acggagagctcctc | cgacgtcggcgtcgcatag | 111 | silent | | high |
| SVP3 | G | T | gtgctgtacttgtcgatga | ccccaggttcttagaatg | 213 | silent | | medium |
| SVP4 | A | G | ttcaagtcaagagaaggctggt | catacttactatgttctaa | 261 | silent | | medium |
| SVP5 | G | A | agactagcttccgcaagc | gcctctcatctgtctaagtcg | 315 | silent | | medium |
| SVP6 | G | C | tcaacccctcaagcccctcg | actgctggagttcatcaaca | 356 | S | T | medium |
| SVP7 | GA | CC | gcttcccgagtgcaacgccgtc | gaaccatcatcgttatcctgt | 619 | E | P | |
| SVP8 | A | G | tctgaaccatcatcgttatc | taatcccaatttcagggatac | 645 | silent | | medium |

These SNPs can be used for mapping of the gene, and for allele association studies and identification of hypomorphic alleles.

4. Ryegrass Transformation System

This invention can be applied to ryegrass *Lolium perenne*, for which we have developed efficient stable transformation system as follows:

Materials florally induced tillers of *Lolium perenne*
Na-hypochlorite (5% available chlorine)
sterile ddH$_2$O 8) Incubate bombarded calli on high osmotic medium LP3-OS for an additional 12-16 hours (overnight) at 25° C. in the dark.
9) Transfer bombarded calli to LP3 medium and incubate for 48 hours at 25° C. in the dark
10) Plate calli on selection medium (LP3+200 mg/l Hygromycin (Hm)). Incubate at 25° C. in the dark on selection medium for two weeks.
11) Transfer all Hm-resistant callus material to regeneration medium MSK+200 mg/l Hm and incubate for four weeks at 25° C. under a 16 hour photoperiod.

12) Transfer developed shoots to MS0+200 mg/l Hm and incubate for another two to four weeks at 25° C. under 16 hour photoperiod.
13) Screen by PCR Hm-resistant plants growing on MS0+200 mg/L Hm.

Microprojectile Bombardment of *Lolium Perenne* with the Bio-Rad Particle Delivery System (PDS-1000/He).

Taken from the PDS-100/He manual. These procedures were developed by Sanford et al. (1992).

Materials and Solutions

---

Bio-Rad Biolistic ® PDS-1000/He Particle Delivery System
Rupture disks (900 PSI)
Macrocarriers
Macrocarrier holders
Microcarriers (1.0 μm)
Stopping screens
Autoclaved 1.5 ml eppendorf tubes
Micropipette tips
Vortex and microfuge
Torque wrench tool
Pen vac
70% Ethanol
Absolute Ethanol
2.5 M $CaCl_2$
100 mM Spermidine

---

(A) Microcarrier Preparation

For 120 bombardments using 500 μg per bombardment.
1. In a 1.5 ml microfuge tube, weigh out 60 mg of microparticles.
2. Add 1 ml of 70% ethanol, freshly prepared.
3. Vortex on a platform vortexer for 3-5 minutes.
4. Incubate for 15 minutes.
5. Pellet the microparticles by spinning for 5 seconds in a microfuge
6. Remove the liquid and discard.
7. Repeat the following steps three times:
   a. Add 1 ml of sterile water
   b. Vortex for 1 minute
   c. Allow the particles to settle for 1 minute
   d. Pellet the microparticles by spinning for 2 seconds in a microfuge.
   e. Remove the liquid and discard.
8. Add sterile 50% glycerol to bring the microparticle concentration to 60 mg/ml (assume no loss during preparation).
9. Store the microparticles at room temperature for up to 2 weeks.

(B) Coating DNA onto Microcarriers

The following procedure is sufficient for six bombardments; if fewer bombardments are needed, prepare enough microcarriers for three bombardments by reducing all volumes by one half. When removing aliquots of microcarriers, it is important to vortex the tube containing the microcarriers continuously in order to maximise uniform sampling.

1. Vortex the microcarriers prepared in 50% glycerol (60 mg/ml) for 5 minutes on a platform vortexer to resuspend and disrupt agglomerated particles.
2. Remove 50 μl (3 mg) of microcarriers to a 1.5 ml microfuge tube.
3. While vortexing vigorously, add in order:
   5 μl DNA (1 μg/μl)
   50 μl $CaCl_2$ (2.5 M)
   20 μl spermidine (0.1 M)
4. Continue vortexing for 2-3 minutes
5. Allow the microcarriers to settle for 1 minute
6. Pellet the microcarriers by spinning for 2 seconds in a microfuge
7. Remove the liquid and discard
8. Add 140 μl of 70% ethanol without disturbing the pellet
9. Remove the liquid and discard
10. Add 140 μl of 100% ethanol without disturbing the pellet
11. Remove the liquid and discard
12. Add 48 μl of 100% ethanol
13. Gently resuspend the pellet by tapping the side of the tube several times, and then by vortexing at low speed for 2-3 seconds
14. Remove six 6 μl aliquots of microcarriers and transfer them to the centre of a macrocarrier. An effort is made to remove equal amounts (500 μg) of microcarriers each time and to spread them evenly over the central 1 cm of the macrocarrier using the pipette tip. Desiccate immediately.

C) Bombardment Procedure
1) Open valve of helium cylinder
2) Adjust helium regulator by turning the helium pressure regulator to 200 PSI above chosen rupture disk (e.g. if a 900 PSI rupture disk will be used, the working pressure has to be adjusted to 1100 PSI)
3) Turn on vacuum pump
4) Place 900 psi rupture disk in the rupture disk-retaining cap. Screw on and tighten retaining cap.
5) Place macrocarriers in sterile macrocarrier holder
6) Place stop screen and macrocarrier holder in the launch assembly, tighten screw lid and place below rupture disk-retaining cap. Launch assembly should be set to a Gap distance of ¼ inch and macrocarrier travel distance of 11 mm.
7) Place tissue sample at a target distance of 90 mm.
8) Turn on main switch of PDS
9) Apply vacuum to 27 inches of Hg
10) Hold vacuum and press "fire" button until shot is performed (automatic)
11) Release "Fire" button and vent chamber
12) After shooting close valve of helium cylinder and loosen pressure valve

TABLE 1

| Compositions of the media used | | | | | |
|---|---|---|---|---|---|
| Media component | LP3 | LP5 | LP3-OS | MSK | MSO |
| Macro elements (mg/l final concentration) | | | | | |
| $KNO_3$ | 1900 | 1900 | 1900 | 1900 | 1900 |
| $NH_4NO_3$ | 1650 | 1650 | 1650 | 1650 | 1650 |
| $CaCl_2 \times 2H_2O$ | 440 | 440 | 440 | 440 | 440 |
| $MgSO_4 \times 2H_2OKH_2PO_4$ | 370 | 370 | 370 | 370 | 370 |
| KCl | 170 | 170 | 170 | 170 | 170 |

TABLE 1-continued

Compositions of the media used

| Media component | LP3 | LP5 | LP3-OS | MSK | MSO |
|---|---|---|---|---|---|
| Micro elements (mg/l final concentration) | | | | | |
| $Na_2EDTA$ | 37.3 | 37.3 | 37.3 | 37.3 | 37.3 |
| $FeSO_4 \times 7H_2O$ | 27.8 | 27.8 | 27.8 | 27.8 | 27.8 |
| $H_3BO_3$ | 6.2 | 6.2 | 6.2 | 6.2 | 6.2 |
| KI | 0.83 | 0.83 | 0.83 | 0.83 | 0.83 |
| $MnSO_4 \times H_2O$ | 16.9 | 16.9 | 16.9 | 16.9 | 16.9 |
| $ZnSO_4 \times 7H_2O$ | 8.6 | 8.6 | 8.6 | 8.6 | 8.6 |
| $CuSO_4 \times 5H_2O$ | 0.025 | 0.025 | 0.025 | 0.025 | 0.025 |
| $Na_2MoO_4 \times 2H_2O$ | 0.25 | 0.25 | 0.25 | 0.25 | 0.25 |
| $CoCl_2 \times 6H_2O$ | 0.025 | 0.025 | 0.025 | 0.025 | 0.025 |
| Carbohydrates (g/l final concentration) | | | | | |
| Maltose | 30 | 30 | 30 | 30 | 30 |
| D-Mannitol | | | 64 | | |
| Hormones (mg/l final concentration) | | | | | |
| 2,4-D | 3.0 | 5.0 | 3.0 | | |
| Kinetin | | | | 0.2 | |
| Vitamins (mg/l final concentration) | | | | | |
| Pyridoxine HCl | 0.5 | 0.5 | 0.5 | 0.5 | |
| Thiamine HCl | 0.1 | 0.1 | 0.1 | 0.1 | |
| Nicotinic acid | 0.5 | 0.5 | 0.5 | 0.5 | |
| Myo-Inositol | 100 | 100 | 100 | 100 | |
| Other organics (mg/l final concentration) | | | | | |
| Glycine | 2 | 2 | 2 | 2 | 2 |

Culture Media

Weights and volumes required of each individual ingredient are specified in Table 1. Adjust media pH to 5.8 with KOH. The addition of a solidifying agent is required. Use agarose (for LP3, LP5 and LP3-OS) and 0.8% (w/v) Agar for MS0 and MSK prior to sterilising. Media LP3, LP5 and MSK are modified from Murashige and Skoog (1962).

Those skilled in the art will appreciate that the invention described above is susceptible to variations and modifications other than those specifically described. It is to be understood that the invention includes all such variations and modifications. The invention also includes all of the steps, features, compositions and products referred to or indicated in this specification, individually or collectively, and any and all combinations of two or more of said steps or features.

REFERENCES

1 Davis, S. J. (2002) Photoperiodism: the coincidental perception of the season. Curr Biol 12 (24), R841-843
2 Araki, T. (2001) Transition from vegetative to reproductive phase. Curr Opin Plant Biol 4 (1), 63-68.
3 Reeves, P. H. and Coupland, G. (2000) Response of plant development to environment: control of flowering by daylength and temperature. Current Opinion in Plant Biology 3 (1), 37-42
4 Colasanti, J. and Sundaresan, V. (2000) 'Florigen' enters the molecular age: long-distance signals that cause plants to flower. Trends Biochem Sci 25 (5), 236-240.
5 Kardailsky, I. et al. (1999) Activation Tagging of the Floral Inducer FT. Science 286 (5446), 1962-1965
6 Kobayashi, Y. et al. (1999) A Pair of Related Genes with Antagonistic Roles in Mediating Flowering Signals. Science 286 (5446), 1960-1962
7 Weigel, D. and Kardailsky, I. (2001) Flowering locus T (FT) and genetically modified plants having modulated flower development. U.S. Pat. No. 6,225,530 The Salk Institute for Biological Studies (La Jolla, Calif.)
8 Bradley, D. J. et al. (1997) Inflorescence commitment and architecture in Arabidopsis. Science 275 (5296), 80-83
9 Bradley, D. et al. (1997) Flowering genes. Patent WO9710339
10 Yano, M. et al. (2001) Genetic control of flowering time in rice, a short-day plant. Plant Physiol 127 (4), 1425-1429
11 Kojima, S. et al. (2002) Hd3a, a rice ortholog of the Arabidopsis FT gene, promotes transition to flowering downstream of Hd1 under short-day conditions. Plant Cell Physiol 43 (10), 1096-1105
12 Yano, M. et al. (2000) Hd1, a major photoperiod sensitivity quantitative trait locus in ride, is closely related to the Arabidopsis flowering time gene CONSTANS. Plant Cell 12 (12), 2473-2484.
13 Takahashi, Y. et al. (2001) Hd6, a rice quantitative trait locus involved in photoperiod sensitivity, encodes the alpha subunit of protein kinase CK2. Proc Natl Acad Sci USA 98 (14), 7922-7927
14 Hayama, R. et al. (2003) Adaptation of photoperiodic control pathways produces short-day flowering in rice. Nature 422 (6933), 719-722
15 Jensen, C. S. et al. (2001) A Terminal Flower1-Like Gene from Perennial Ryegrass Involved in Floral Transition and Axillary Meristem Identity. Plant Physiol 125 (3), 1517-1528.
16 Emmerlin, M. et al. (2002) MANIPULATION OF FLOWERING AND PLANT ARCHITECTURE. Patent WO0233091 AGRICULTURE VICTORIA SERV PTY 17 Fowler, S. et al. (1999) GIGANTEA: a circadian clock-controlled gene that regulates photoperiodic flowering in *Arabidopsis* and encodes a protein with several possible membrane-spanning domains. Embo J 18 (17), 4679-4688.
18 Coupland, G. et al. (1999) PLANT CONTROL GENES. Patent WO9949064
19 Huq, E. et al. (2000) GIGANTEA is a nuclear protein involved in phytochrome signaling in *Arabidopsis*. Proc Natl Acad Sci USA 97 (17), 9789-9794.
20 Park, D. H. et al. (1999) Control of circadian rhythms and photoperiodic flowering by the *Arabidopsis* GIGANTEA gene. Science 285 (5433), 1579-1582.
21 Michaels, S. D. and Amasino, R. M. (1999) FLOWERING LOCUS C Encodes a Novel MADS Domain Protein That Acts as a Repressor of Flowering. Plant Cell 11 (5), 949-956
22 Sheldon, C. C. et al. (1999) The FLF MADS box gene. A repressor of flowering in *arabidopsis* regulated by vernalization and methylation. Plant Cell 11 (3), 445-458
23 Michaels, S. D. et al. (2003) AGL24 acts as a promoter of flowering in *Arabidopsis* and is positively regulated by vernalization. Plant J 33 (5), 867-874
24 Scortecci, K. C. et al. (2001) Identification of a MADS-box gene, FLOWERING LOCUS M, that represses flowering. Plant J 26 (2), 229-236
25 Michaels, S. et al. (2000) ALTERATION OF FLOWERING TIME IN PLANTS. Patent WO0050615 WISCONSIN ALUMNI RES FOUND (US)
26 Hartmann, U. et al. (2000) Molecular cloning of SVP: a negative regulator of the floral transition in *arabidopsis*. Plant J 21 (4), 351-360
27 Lee, H. et al. (2000) The AGAMOUS-LIKE 20 MADS domain protein integrates floral inductive pathways in *Arabidopsis*. Genes Dev 14 (18), 2366-2376.
28 Michaels, S. D. and Amasino, R. M. (2001) Loss of flowering locus c activity eliminates the late-flowering phenotype of frigida and autonomous pathway mutations but not responsiveness to vernalization. Plant Cell 13 (4), 935-942.
29 Reeves, P. H. and Coupland, G. (2001) Analysis of flowering time control in *arabidopsis* by comparison of double and triple mutants. Plant Physiol 126 (3), 1085-1091
30 Frohman, M. A. et al. (1988) Rapid production of full-length cDNAs from rare transcripts: amplification using a single gene-specific oligonucleotide primer. Proc Natl Acad Sci USA 85 (23), 8998-9002
31 Ohara, O. et al. (1989) One-sided polymerase chain reaction: the amplification of cDNA. Proc Natl Acad Sci USA 86 (15), 5673-5677
32 Loh, E. Y. et al. (1989) Polymerase chain reaction with single-sided specificity: analysis of T cell receptor delta chain. Science 243 (4888), 217-220
33 Ratcliffe, O. J. et al. (1998) A common mechanism controls the life cycle and architecture of plants. Development 125 (9), 1609-1615
34 Saedler, H. et al. (2000) TRANSGENIC PLANTS EXHIBITING AN ALTERED FLOWERING TIME. Patent EP1055729
35 Yu, H. et al. (2002) AGAMOUS-LIKE 24, a dosage-dependent mediator of the flowering signals. Proc Natl Acad Sci USA 99 (25), 16336-16341

The invention claimed is:

1. A substantially purified or isolated nucleic acid comprising a nucleotide sequence selected from the group consisting of
   (a) SEQ ID NO: 1;
   (b) SEQ ID NO: 2; and
   (c) variants of the sequences recited in (a) and (b), said variants consisting of the sequence recited in (a) or (b), respectively, with one or more nucleic acid changes, said changes consisting of nucleic acid substitutions that result in conservative amino acids substitutions, with the proviso that the variant has at least 95% identity to the sequence recited in (a) or (b), respectively.

2. A substantially purified or isolated nucleic acid comprising a nucleotide sequence selected from the group consisting of SEQ ID NO: 1 and SEQ ID NO: 2.

3. A substantially purified or isolated nucleic acid comprising SEQ ID NO: 2.

4. A substantially purified or isolated nucleic acid comprising SEQ ID NO: 1.

5. A construct including one or more nucleic acids according to claim 1.

6. The construct according to claim 5 wherein the one or more nucleic acids are operably linked to one or more regulatory elements different from regulatory elements associated with a gene encoding Seq ID No. 21 in naturally occurring ryegrass, such that the one or more nucleic acids are each expressed.

7. The construct according to claim 6, wherein the one or more regulatory elements include a promoter and a terminator, said promoter, nucleic acid and terminator being operatively linked, and wherein at least one of the promoter and terminator is different from regulatory elements associated with a gene encoding Seq ID No. 21 in naturally occurring ryegrass.

8. A monocotyledonous or dicotyledonous plant cell, plant, plant seed or other plant part, transformed with the construct according to claim 5.

9. A monocotyledonous or dicotyledonous plant, plant seed or other plant part derived from the plant cell or plant according to claim 8, and harboring the construct.

10. A method of modifying flowering in a monocotyledonous or dicotyledonous plant, said method including introducing into said plant an effective amount of the nucleic acid according to claim 1, or the construct according to claim 5.

11. A preparation for transforming a monocotyledonous or dicotyledonous plant comprising the nucleic acid according to claim 1, or the construct according to claim 5.

\* \* \* \* \*

SEQUENCE LISTING

```
<160> NUMBER OF SEQ ID NOS: 46

<210> SEQ ID NO 1
<211> LENGTH: 393
<212> TYPE: DNA
<213> ORGANISM: Lolium perenne

<400> SEQUENCE: 1
tgtatctttt gggactgagg ttgtgtgcta cgagagccct cggccggtgc tcgggatcca      60
ccggctggtg tttctgctct tccaacagct cggccgtcag accgtytacg ctccgggctg     120
gcggcagaat tcagcaccc gcgacttcgc cgagctgtac aacctcggct cgccggtcgc      180
cgccgtctac ttcaactgcc aaagggagtc gggaactggt ggaaggagga tgtgaattct     240
ctgacactag tcgtcaaccc gtgcgcctgc acaggctagt aattggtgaa atcgaatcat     300
ggagccaaaa aggagttgtt tccaaattta attgtgaaaa tggttttgat tttcattata     360
tatagaatta tatttaaaaa aaaaaaaaaa aaa                                  393

<210> SEQ ID NO 2
<211> LENGTH: 340
<212> TYPE: DNA
<213> ORGANISM: Lolium perenne

<400> SEQUENCE: 2
tgtatctttt gggactgagg ttgtgtgcta cgagagccct cggccggtgc tcgggatcca      60
ccggctggtg tttctgctct tccaacagct cggccgtcag accgtttacg ctccgggctg     120
gcggcagaat tcagcaccc gcgacttcgc cgagctgtac aacctcggct cgccggtcgc      180
cgccgtctac ttcaactgcc aaagggagtc gggaactggt ggaaggagga tgtgaattct     240
```

```
ctgacatatt atgaccatat aggttgagcg tggatgattg tatcgggggt tatacgtggc    300
taaatgaaaa aagatcattg taataaaaaa aaaaaaaaaa                         340
```

<210> SEQ ID NO 3
<211> LENGTH: 381
<212> TYPE: DNA
<213> ORGANISM: Lolium perenne

<400> SEQUENCE: 3

```
ggtaaattct actcattgtg tatgactgat ccggccgcac cgagcaggaa agaacctaaa     60
ttcagggaat ggcatcattg gctcgtaggc aatgtcccag aatgtgatgt agccaagggc    120
gaaactttat ccgaatatat tggctctgga cctcccccag atactggact tcatcgttat    180
gttttcctcg tctaccttca gccgggtaaa atcgatttca aagatgtgcc acgtttgacc    240
aacagatctg gtgacaatcg tgccaatttt aaaattcaag cttttcgccga taaatataat    300 ttgggcgatc cggtggcctc agcttattat cgagccgaat acgacgacta cgtgccaatt    360
ttgtacaaac aattgggagc a                                              381
```

<210> SEQ ID NO 4
<211> LENGTH: 965
<212> TYPE: DNA
<213> ORGANISM: Lolium perenne

<400> SEQUENCE: 4

```
gcagcagcac atacacaatt acctgagctt ccattcagca agaggaaca cacgcacact     60 gatcatccct cgggttccga tttcaaggca tcaacatgtc aagggcgttg gagcctctcg    120
ttgtggggaa ggtgattggt gaggtgctgg acagcttcaa ccccaccgtg aagatgacgg    180
caacctacag ctccaacaag caggtgttca acggccatga gttcttcccc tcggccatcg    240
ccgctaagcc gcgtgtcgag gttcaggggg gcgaccttag atccttcttc acattggtga    300
tgactgaccc tgatgtgcca ggacccagtg atccgtacct gagggagcat cttcactgga    360
ttgttactga tattcctggg actactgatg cttcttttgg gaaggaggtg gtgcactacg    420
agagcccaaa gccaaacatc ggcatccaca ggttcatcct cgtgctgttc agcagacgc    480 accggggctc ggtaaagaac acaccgtcgt cgagggaccg cttcaggacc cgcgagttcg    540
ccaaggataa cgagctcggc ctccctgtcg cygctgtcta cttcaacgcg cagcgggaga    600
ccgccgcccg ccggcgatag ctcaacggca accgaaccaa ccaaccagca cacccccct    660 actatgtacc tgatctagct acatgataaa acgaactgcg tacaatcacc tattagctag    720
cttcgatggc ctttcctgct acatccaagc atgcacaatg tctgaataaa acacaccggt    780
aaattagctg tttgcacgag aaagctgctc cytactagta cgtagccgtt gcccatttag    840
ttaatttttg tgaatgtgac aagatcgatg attgggaaga gattgcagtg ttgactgaga    900
aaaaagtgca agatttgaag caataatagt cgtcagggag taaaaaaaaa aaaaaaaaa    960 aaaaa                                                                965
```

<210> SEQ ID NO 5
<211> LENGTH: 811
<212> TYPE: DNA
<213> ORGANISM: Lolium perenne

<400> SEQUENCE: 5

```
aacaaccatg aggttatatt tcctcattcc tcaagactgt ttacctagtg cttcgacttg     60
ctagttacct gtcagctgta gatatttggc atcgatcatc accacctttt cagttcaagt    120
```

```
tagctagcta gacatggcta gggtggtgga gcctctcatc gtcggaaagg tgatcgggga      180
ggtcatcgac aacttcaccc ccactgagaa gatgacagta acctacagct ccaacaagca      240
ggtgttcaat ggccacgaat tcttcccgtc ggcagtcgtc tccaagccac gcattgaggt      300
ccagggtggc gacatgagat ccttcttcac actggtcatg acggacccag atgtgccagg      360
gcctagcgac ccatacctga gggagcatct ccactggatc gtcaataata ttccaggcac      420
cactgatgct tcttttggaa aggaggtggt gagctacgag agcccaagc ccaacatcgg       480 cattcacagg ttcaccttcg tgctgttcaa gcagaagcag cggcagacaa tgagccctcc      540
ctccagcagg gactacttca acactcgccg cttcgctgcc gcgaacgatc ttggcctccc      600
agtcgctgcc gtctacttca acgcgcagcg ggagacagct gcgcgccgcc gctgatggaa      660
acaatcagcg aaaccttct tctcgcgcat gcatggcgca tgcatgcaat cctatggatc       720
aaccaatagc tctactacta gctaccctt atgtctttca ttcaaataag agtttgcttg       780
tgagcgtctt gtgtcaaaaa aaaaaaaaaa a                                     811
```

<210> SEQ ID NO 6
<211> LENGTH: 3768
<212> TYPE: DNA
<213> ORGANISM: Lolium perenne

<400> SEQUENCE: 6

```
tcgactggag cacgaggaca ctgacatgga ctgaaggagt agaaacccca accacgttac       60
ggatgaaaaa atcttttttct cgcctctcct cgcccctcgc tccaagcttc tctctcctcg     120
ccgtctaccg ctcgccgccg ccgctgattc gccgccggag ccacggagta gagcgcgccc     180
agtctaggat cttaaactaa taagtatgyc tgtctcaaat gggaagtgga tcgacgggct     240
ccagttctct tcactattct ggcccccgcc acacgatgca cagcagaaac aggcacaaac     300
tttggcctac gttgagtact ttggtcagtt tacatctgac agtgagcaat tcccggagga     360
tgtagctcag ctcatccaaa gttactatcc atcgaaagaa aaacgcttgg tagatgaagt     420
attagcaacc tttgttctcc atcaccccga gcatggtcat gcagttgtac atccaattct     480
ttcacgcatc atagatgggt ccctgagtta tgatagacat ggttccccat tcaattcttt     540
catctcttta tttacccaaa ctgctgagaa agagtattca gagcagtggg ctttggcgtg     600
tggagaaatt cttagagttc ttactcacta caataggcca atcttcaaag ttgcagaatg     660
taacgacacc tccgaccagg ccacaacaag ttattcctta catgacaaag ctaatagctc     720
tccagaaaat gaacctgaac ggaagccatt gaggccatta tctccttgga tcacagacat     780
tttgttaaat gcacctttgg gcattagaag tgactatttt agatggtgtg gtggagtcat     840
gggaaaatac gcagctggtg gagaactgaa gcctccaaca actgcttaca gccgggggagc     900 tggtaagcat ccacaactta tgccatccac ccctagatgg gctgttgcca atggagctgg     960
agtcatcwta wgtgtctgtg acgaggaagt agctcgttac gagacagcaa acttaaccgc    1020
agcagctgtt cctgsgcttc tgctacctcc accgacaatg cccttggatg agcatttggt    1080
ggcagggttg cccctcttg aaccatacgc tcgcttgttt cacagatact aygcaattgc     1140
tactccaagt gctacacara ggttgctctt tggtcttctt gaagcaccgc cttcatgggc    1200
tccagatgca cttgatgcag cagtacagct tgttgaactc cttcgagcag ccgaagatta    1260
tgctactggc atgcggcttc cgaaaaattg gctgcatcct catttcttgc gtgcaatcgg    1320
aactgcaatg tctatgagag ctggyatggc tgctgatacg gccgctgcct tgctatttcg    1380
```

```
tatactatcc caaccaacgt tgcttttcc tccactaaga catgccgaag gagttgtgca    1440
gcatgaacca ctaggtggct atgtatcatc atacaaaaga cagctggara ttcctgcatc    1500
tgaaaccact attgatgcta ctgcacaagg cattgcttcc ttgctgtgyg ctcatggtcc    1560
tgatgttgak tggagaatat gtaccatctg ggaagctgcc tatggtttgt tacctctgaa    1620
ttcrtcagca gtcgatttgc ctgaaattgt tgtagctgct ccgcttcagc cacctacttt    1680
atcatggagc ctatatttgc cactgttgaa agtatttgag tatctacctc gtggaagtcc    1740
atctgaagca tgccttatga gaatatttgt ggcaactgtt gaagctatac tcaggagaac    1800
tttcccttcg gaaaccgaac catccaaaaa accaagaagt ccatctaaga gccttgctgt    1860
tgctgaactc cgtacgatga tacattcact ctttgttgaa tcatgtgcct caatgaacct    1920
tgcttcgcgg ttattgtttg tagtattgac tgtctcagtc agtcatcaag ctctgccggg    1980
gggcagcaaa agacctacag gcagtgagaa ccattcttct gaggagtcca ctgaggactc    2040
aaaattaacc aatggaagaa acagatgcaa gaagaaacaa gggcctgttg gtaccttga    2100
ctcgtatgtg ctggctgctg tttgtgcttt atcttgtgag cttcagctgt tccctatact    2160
ttgcaagaat gttacgaaga caaacataaa agactctata aagattacca tgcctggaaa    2220
aaccaatggg atcagtaatg agctacacaa tagcgttaac tcagcgattc tccatactcg    2280
tagaattctt ggcatcctgg aagctctttt ctccttgaag ccatcatcag ttggtacctc    2340
ctggagctat agttcaaatg agatagttgc agcagcaatg gttgctgctc atgtttctga    2400
gttattccgt aggtcgaggc catgcctaaa tgcactatct gcactgaagc gatgtaagtg    2460
ggatgctgag atttctacca gggcatcatc gctttaccat ctgatcgact tgcatggtaa    2520
aactgtgtca tccatcgtga acaaagctga gcctttggaa gctcacctga accttacagc    2580
agtaaagaaa gatgatcaac accacattga ggaaagcaat accagctcat cggattatgg    2640
gaacttggag aagaagagta agaaaaatgg ttttttcaaga ccactcatga aatgtgcaga    2700
acaggctagg agaaatggta acgttgcaag tacatcgggg aaagctactg caactttaca    2760
ggcggaagca tctgatttgg caaacttcct taccatggac aggaacgggg gttatggagg    2820
ttctcaaact ctcctaagaa ctgtaatgtc agaaaagcag gaactatgct tttctgttgt    2880
ctcgttgctg tggcataagc ttattgcatc tcccgaaaca cagatgtctg cagagagtac    2940
atcagctcat cagggttgga gaaaggttgc agatgcgctt tgtgatgttg tttcagcttc    3000
accggccaag gcthcaactg ctattgtcct gcaggctgag aaggacttgc agccctggat    3060
tgctcgagat gatgagcaag gtcagaagat gtggagagtc aaccagcgaa tagtgaaact    3120
gatagctgag cttatgagga accatgatag cccagaagca ctgataattc ttgcgagcgc    3180
ttcagacctt ctgctccgtg ccacggatgg gatgcttgtt gatggtgaag cttgtacctt    3240
gcctcaattg gagcttctgg aagtaaccgc cagagccatt catctcatcg ttgaatgggg    3300
agatccaggt gtagcagttg ctgatggcct ctcgaatctg ctgaagtgcc ggctatcacc    3360
taccatccga tgcctttccc accctagtgc acatgtacgg gcgctcagca tgtccgtcct    3420
tcgcgacatc ttgaacagtg gaccaataag ttccaccaag ataattcaag gagagcagcg    3480
gaacggcatc caaagcccaa gttaccggtg cgcggcagca gtatgaccaa actggcaagc    3540
ggacgtcgag agatgcatag agtgggaagc ccacaaccgt caggccaccg ggatgacgct    3600
tgccttttctc actgcagckg ctaacgaact cggatgcccc cttccttgct gacacagcca    3660
tatttgaagc tgrcatcggc gayacttgac rgttagcgcg agcagttgct gcatggtcag    3720
cgagcaggat ggctaatccy tkgctcaagg atgacttccc agtctgaa              3768
```

```
<210> SEQ ID NO 7
<211> LENGTH: 1148
<212> TYPE: PRT
<213> ORGANISM: Lolium perenne
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (255)..(256)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
<220> FEATURE:
<221> NAME/KEY: misc_feature
<222> LOCATION: (455)..(455)
<223> OTHER INFORMATION: Xaa can be any naturally occurring amino acid
<220> FEATURE:
<221> NAME/KEY: misc_feature
<222> LOCATION: (937)..(937)
<223> OTHER INFORMATION: Xaa can be any naturally occurring amino acid

<400> SEQUENCE: 7

Met Xaa Val Ser Asn Gly Lys Trp Ile Asp Gly Leu Gln Phe Ser Ser
1               5                   10                  15

Leu Phe Trp Pro Pro His Asp Ala Gln Gln Lys Gln Ala Gln Thr
            20                  25                  30

Leu Ala Tyr Val Glu Tyr Phe Gly Gln Phe Thr Ser Asp Ser Glu Gln
        35                  40                  45

Phe Pro Glu Asp Val Ala Gln Leu Ile Gln Ser Tyr Tyr Pro Ser Lys
50                  55                  60

Glu Lys Arg Leu Val Asp Glu Val Leu Ala Thr Phe Val Leu His His
65                  70                  75                  80

Pro Glu His Gly His Ala Val Val His Pro Ile Leu Ser Arg Ile Ile
                85                  90                  95

Asp Gly Ser Leu Ser Tyr Asp Arg His Gly Ser Pro Phe Asn Ser Phe
            100                 105                 110

Ile Ser Leu Phe Thr Gln Thr Ala Glu Lys Glu Tyr Ser Glu Gln Trp
        115                 120                 125

Ala Leu Ala Cys Gly Glu Ile Leu Arg Val Leu Thr His Tyr Asn Arg
    130                 135                 140

Pro Ile Phe Lys Val Ala Glu Cys Asn Asp Thr Ser Asp Gln Ala Thr
145                 150                 155                 160

Thr Ser Tyr Ser Leu His Asp Lys Ala Asn Ser Ser Pro Glu Asn Glu
                165                 170                 175

Pro Glu Arg Lys Pro Leu Arg Pro Leu Ser Pro Trp Ile Thr Asp Ile
            180                 185                 190

Leu Leu Asn Ala Pro Leu Gly Ile Arg Ser Asp Tyr Phe Arg Trp Cys
        195                 200                 205

Gly Gly Val Met Gly Lys Tyr Ala Ala Gly Gly Glu Leu Lys Pro Pro
    210                 215                 220

Thr Thr Ala Tyr Ser Arg Gly Ala Gly Lys His Pro Gln Leu Met Pro
225                 230                 235                 240

Ser Thr Pro Arg Trp Ala Val Ala Asn Gly Ala Gly Val Ile Xaa Xaa
                245                 250                 255

Val Cys Asp Glu Glu Val Ala Arg Tyr Glu Thr Ala Asn Leu Thr Ala
            260                 265                 270
```

-continued

Ala Ala Val Pro Xaa Leu Leu Pro Pro Thr Met Pro Leu Asp
        275                 280             285

Glu His Leu Val Ala Gly Leu Pro Pro Leu Glu Pro Tyr Ala Arg Leu
    290                 295             300

Phe His Arg Tyr Tyr Ala Ile Ala Thr Pro Ser Ala Thr Gln Arg Leu
305                     310             315                 320

Leu Phe Gly Leu Leu Glu Ala Pro Pro Ser Trp Ala Pro Asp Ala Leu
                325                 330                 335

Asp Ala Ala Val Gln Leu Val Glu Leu Leu Arg Ala Ala Glu Asp Tyr
            340                 345                 350

Ala Thr Gly Met Arg Leu Pro Lys Asn Trp Leu His Leu His Phe Leu
        355                 360                 365

Arg Ala Ile Gly Thr Ala Met Ser Met Arg Ala Gly Met Ala Ala Asp
    370                 375                 380

Thr Ala Ala Leu Leu Phe Arg Ile Leu Ser Gln Pro Thr Leu Leu
385                     390                 395             400

Phe Pro Pro Leu Arg His Ala Glu Gly Val Val Gln His Glu Pro Leu
                405                 410                 415

Gly Gly Tyr Val Ser Ser Tyr Lys Arg Gln Leu Glu Ile Pro Ala Ser
            420                 425                 430

Glu Thr Thr Ile Asp Ala Thr Ala Gln Gly Ile Ala Ser Leu Leu Cys
        435                 440                 445

Ala His Gly Pro Asp Val Xaa Trp Arg Ile Cys Thr Ile Trp Glu Ala
    450                 455                 460

Ala Tyr Gly Leu Leu Pro Leu Asn Ser Ser Ala Val Asp Leu Pro Glu
465                 470                 475                 480

Ile Val Val Ala Ala Pro Leu Gln Pro Pro Thr Leu Ser Trp Ser Leu
                485                 490                 495

Tyr Leu Pro Leu Leu Lys Val Phe Glu Tyr Leu Pro Arg Gly Ser Pro
            500                 505                 510

Ser Glu Ala Cys Leu Met Arg Ile Phe Val Ala Thr Val Glu Ala Ile
        515                 520                 525

Leu Arg Arg Thr Phe Pro Ser Glu Thr Glu Pro Ser Lys Lys Pro Arg
    530                 535                 540

Ser Pro Ser Lys Ser Leu Ala Val Ala Glu Leu Arg Thr Met Ile His
545                 550                 555                 560

Ser Leu Phe Val Glu Ser Cys Ala Ser Met Asn Leu Ala Ser Arg Leu
                565                 570                 575

Leu Phe Val Val Leu Thr Val Ser Val Ser His Gln Ala Leu Pro Gly
            580                 585                 590

Gly Ser Lys Arg Pro Thr Gly Ser Glu Asn His Ser Ser Glu Glu Ser
        595                 600                 605

Thr Glu Asp Ser Lys Leu Thr Asn Gly Arg Asn Arg Cys Lys Lys Lys
    610                 615                 620

Gln Gly Pro Val Gly Thr Phe Asp Ser Tyr Val Leu Ala Ala Val Cys
625                 630                 635                 640

Ala Leu Ser Cys Glu Leu Gln Leu Phe Pro Ile Leu Cys Lys Asn Val
                645                 650                 655

Thr Lys Thr Asn Ile Lys Asp Ser Ile Lys Ile Thr Met Pro Gly Lys
            660                 665                 670

Thr Asn Gly Ile Ser Asn Glu Leu His Asn Ser Val Asn Ser Ala Ile
        675                 680                 685

```
Leu His Thr Arg Arg Ile Leu Gly Ile Leu Glu Ala Leu Phe Ser Leu
690             695                 700

Lys Pro Ser Ser Val Gly Thr Ser Trp Ser Tyr Ser Ser Asn Glu Ile
705                 710                 715                 720

Val Ala Ala Ala Met Val Ala His Val Ser Glu Leu Phe Arg Arg
            725                 730                 735

Ser Arg Pro Cys Leu Asn Ala Leu Ser Ala Leu Lys Arg Cys Lys Trp
                740                 745                 750

Asp Ala Glu Ile Ser Thr Arg Ala Ser Ser Leu Tyr His Leu Ile Asp
                755                 760                 765

Leu His Gly Lys Thr Val Ser Ser Ile Val Asn Lys Ala Glu Pro Leu
770                 775                 780

Glu Ala His Leu Asn Leu Thr Ala Val Lys Lys Asp Gln His His
785                 790                 795                 800

Ile Glu Glu Ser Asn Thr Ser Ser Ser Asp Tyr Gly Asn Leu Glu Lys
                805                 810                 815

Lys Ser Lys Lys Asn Gly Phe Ser Arg Pro Leu Met Lys Cys Ala Glu
            820                 825                 830

Gln Ala Arg Arg Asn Gly Asn Val Ala Ser Thr Ser Gly Lys Ala Thr
            835                 840                 845

Ala Thr Leu Gln Ala Glu Ala Ser Asp Leu Ala Asn Phe Leu Thr Met
850                 855                 860

Asp Arg Asn Gly Gly Tyr Gly Gly Ser Gln Thr Leu Leu Arg Thr Val
865                 870                 875                 880

Met Ser Glu Lys Gln Glu Leu Cys Phe Ser Val Val Ser Leu Leu Trp
            885                 890                 895

His Lys Leu Ile Ala Ser Pro Glu Thr Gln Met Ser Ala Glu Ser Thr
                900                 905                 910

Ser Ala His Gln Gly Trp Arg Lys Val Ala Asp Ala Leu Cys Asp Val
            915                 920                 925

Val Ser Ala Ser Pro Ala Lys Ala Xaa Thr Ala Ile Val Leu Gln Ala
            930                 935                 940

Glu Lys Asp Leu Gln Pro Trp Ile Ala Arg Asp Asp Glu Gln Gly Gln
945                 950                 955                 960

Lys Met Trp Arg Val Asn Gln Arg Ile Val Lys Leu Ile Ala Glu Leu
                965                 970                 975

Met Arg Asn His Asp Ser Pro Glu Ala Leu Ile Ile Leu Ala Ser Ala
            980                 985                 990

Ser Asp Leu Leu Leu Arg Ala Thr Asp Gly Met Leu Val Asp Gly Glu
        995                 1000                1005

Ala Cys Thr Leu Pro Gln Leu Glu Leu Leu Glu Val Thr Ala Arg
    1010                1015                1020

Ala Ile His Leu Ile Val Glu Trp Gly Asp Pro Gly Val Ala Val
    1025                1030                1035

Ala Asp Gly Leu Ser Asn Leu Leu Lys Cys Arg Leu Ser Pro Thr
    1040                1045                1050

Ile Arg Cys Leu Ser His Pro Ser Ala His Val Arg Ala Leu Ser
    1055                1060                1065

Met Ser Val Leu Arg Asp Ile Leu Asn Ser Gly Pro Ile Ser Ser
    1070                1075                1080

Thr Lys Ile Ile Gln Gly Glu Gln Arg Asn Gly Ile Gln Ser Pro
    1085                1090                1095

Ser Tyr Arg Cys Ala Ala Ala Ser Met Thr Asn Trp Gln Ala Asp
```

| | | | |
|---|---|---|---|
| | 1100 | 1105 | 1110 |

Val Glu Arg Cys Ile Glu Trp Glu Ala His Asn Arg Gln Ala Thr
    1115                   1120                   1125

Gly Met Thr Leu Ala Phe Leu Thr Ala Ala Ala Asn Glu Leu Gly
    1130                   1135                   1140

Cys Pro Leu Pro Cys
    1145

```
<210> SEQ ID NO 8
<211> LENGTH: 2652
<212> TYPE: DNA
<213> ORGANISM: Lolium perenne
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (2583)..(2583)
<223> OTHER INFORMATION: n is a, c, g, or t
<220> FEATURE:
<221> NAME/KEY: misc_feature
<222> LOCATION: (2649)..(2649)
<223> OTHER INFORMATION: n is a, c, g, or t

<400> SEQUENCE: 8
```

| | |
|---|---:|
| aanttgtaca cgatttcact atagtggcga attgggccct ctatatgcat gctcgagcgg | 60 |
| ccgccagtgt gatggatatc tgcagaattc ttnaacatgt gctaaagtga tatcaccgct | 120 |
| taacccggga gatatacgta cgagctcgcc ggcggtcaca ctacctatag acgtcttaag | 180 |
| ggccctttym tmyyyctcct ctcctttcgc atccccaacc gcaccactgt gcctctccga | 240 |
| ccccggccgg ccgacgcgcg ctacgcctct ccgggaaark akrrrgagga gaggaaagcg | 300 |
| taggggttgg cgtggtgaca cggagaggct ggggccggcc ggctgcgcgc gatgcggaga | 360 |
| cggcgtgdgg actggggrgg rrggaggaga kmgatcgatc rgtygggyys ggaggcggcg | 420 |
| atggcgcggg agaggcgcga gatcaagcgg gccgcachcc tgaccccycc yyccctcctct | 480 |
| mkctagctag ycarcccrrs cctccgccgc taccgcgccc tctccgcgct ctagttcgcc | 540 |
| atagagagcg cggcggcgcg ccaggtcacc ttctccaagc gccgcagggg cctcttcaag | 600 |
| aaggccgagg agctctccgt cctatgcgac tatctctcgc gccgccgcgc ggtccagtgg | 660 |
| aagaggttcg cggcgtcccc ggagaagttc ttccggctcc tcgagaggca ggatacgctg | 720 |
| gccgacgtcg cgctcatcgt cttctcgtcc acagggaagc tctcccagtt cgcaagctcc | 780 |
| agtatgaatg agatcatcga caagtacagc cggctgcagc gcgagtagca gaagagcagg | 840 |
| tgtcccttcg agagggtcaa gcgttcgagg tcatacttac tctagtagct gttcatgtcg | 900 |
| acccattcta agaacctggg gaaagcagac cagccttctc ttgacttgaa tttagaacat | 960 |
| agtaagtatg caaatctgaa cgatcagctt tgggtaagat tcttggaccc ctttcgtctg | 1020 |
| gtcggaagag aactgaactt aaatcttgta tcattcatac gtttagactt gctagtcgaa | 1080 |
| gcggaagcta gtctycgact tagacagatg agaggcgagg ggcttgaggg gttgavtgtt | 1140 |
| gatgaactcc agcagttgga gaagaacctt cgccttcgat cagargctga atctgtctac | 1200 |
| tctccgctcc ccgaactccc caactbacaa ctacttgagg tcgtcaacct cttcttggaa | 1260 |
| gaaactggtc tgcacagggt gcttcagacg aaagatcaac aattcttgga gcagatcaat | 1320 |

-continued

```
gaattgcaac gaaagagctc acagctggca ctttgaccag acgtgtccca cgaagtctgc      1380
tttctagttg ttaagaacct cgtctagtta cttaacgttg cttctcgag tgtcgaccgt       1440
gaggagaaca tgcaactgag gaaccaagta tcccagatac caatagctgg caagccagta      1500
gttgctgata ccgaaaatgt tattgctgag ctcctcttgt acgttgactc cttggttcat      1560
agggtctatg gttatcgacc gttcggtcat caacgactat ggcttttaca ataacgactc      1620
gatgggcagt cctctgaatc tgtcatgacg gcgttgcact cgggaagctc acaggataac      1680
gatgatggtt cagatgtatc cctgaaattg ctacccgtca ggagacttag acagtactgc      1740
cgcaacgtga gcccttcgag tgtcctattg ctactaccaa gtctacatag ggactttaac      1800
ggattaccct gcagtgcgtg gaagtaacta tataaaaycg tcrsttcaga tctttatgga      1860
actgcccacr tcagtggaga agctcttgtg cctaatggga cgtcacgcac cttcattgat      1920
atattttrgc agysaagtct agaaatacct tgacgggtgy agtcacctct tcgagaacac      1980
taatcsacaa acgtaccyga gctgcaataa tcttgcrgct gaagcgagat cagttaacct      2040
gatttatcat ccttgtggct gcatgacgtg attagstgtt tgcatggrct cgacgttatt      2100
agaacgycga cttcgctcta gtcaattgga ctaaatagta ggaacaccga cgtactgcac      2160
atgttcccgt tyttacygtt tactaggatg ttaactaaac ttttagatcg atctgatgtc      2220
catcttatcc ccgttggcac tatttgttca tacaagggca araatgrcaa atgatcctac      2280
aattgatttg aaaatctagc tagactacag gtagaatagg ggcaaccgtg ataaacaagt      2340
tggtatccat gtaccttaac tgtcagtata tcttaaamtt atggtctata wwtkcwyywg      2400
crabrytarb yrrmvdtwyg rtctrvtrrm accataggta catggaattg acagtcatat      2460
agaatttkaa taccagatat wwamgwrrwc gytvyratyv ryykbhawrc yagaybayyk      2520
dvmrmrmwma rwavmawrma wrdaragggg ccaattcgcc ctatagtgaa tcgtggtaca      2580
aanttchbky kykwktywtb ktwyktwyht ytccccggtt aagcgggata tcacttagca      2640
ccatgtttna ag                                                         2652
```

<210> SEQ ID NO 9
<211> LENGTH: 228
<212> TYPE: PRT
<213> ORGANISM: Lolium perenne
<220> FEATURE:
<221> NAME/KEY: misc_feature
<222> LOCATION: (119)..(119)
<223> OTHER INFORMATION: Xaa can be any naturally occurring amino acid

<400> SEQUENCE: 9

Met Ala Arg Glu Arg Arg Glu Ile Lys Arg Ile Glu Ser Ala Ala Ala
1               5                   10                  15

Arg Gln Val Thr Phe Ser Lys Arg Arg Arg Gly Leu Phe Lys Lys Ala
            20                  25                  30

Glu Glu Leu Ser Val Leu Cys Asp Ala Asp Val Ala Leu Ile Val Phe
        35                  40                  45

Ser Ser Thr Gly Lys Leu Ser Gln Phe Ala Ser Ser Met Asn Glu
    50                  55                  60

Ile Ile Asp Lys Tyr Ser Thr His Ser Lys Asn Leu Gly Lys Ala Asp
65                  70                  75                  80

Gln Pro Ser Leu Asp Leu Asn Leu Glu His Ser Lys Tyr Ala Asn Leu
                85                  90                  95

Asn Asp Gln Leu Ala Glu Ala Ser Leu Arg Leu Arg Gln Met Arg Gly
            100                 105                 110

```
Glu Gly Leu Glu Gly Leu Xaa Val Asp Glu Leu Gln Gln Leu Glu Lys
            115                 120                 125

Asn Leu Glu Thr Gly Leu His Arg Val Leu Gln Thr Lys Asp Gln Gln
        130                 135                 140

Phe Leu Glu Gln Ile Asn Glu Leu Gln Arg Lys Ser Ser Gln Leu Ala
145                 150                 155                 160

Glu Glu Asn Met Gln Leu Arg Asn Gln Val Ser Gln Ile Pro Ile Ala
                165                 170                 175

Gly Lys Pro Val Val Ala Asp Thr Glu Asn Val Ile Ala Glu Asp Gly
            180                 185                 190

Gln Ser Ser Glu Ser Val Met Thr Ala Leu His Ser Gly Ser Ser Gln
        195                 200                 205

Asp Asn Asp Asp Gly Ser Asp Val Ser Leu Lys Leu Gly Leu Pro Cys
210                 215                 220

Ser Ala Trp Lys
225
```

<210> SEQ ID NO 10
<211> LENGTH: 683
<212> TYPE: DNA
<213> ORGANISM: Lolium perenne

<400> SEQUENCE: 10

```
tggcgmggga gaggcgcgag atcaagcgga tagagagcgc ggcggcgcgc caggtcacct      60
tctccaagcg ccgcaggggc ctcttcaaga aggccgagga gctctccgtm ctatgcgacg     120
ccgacgtcgc gctcatcgtc ttctcgtcca cagggaagct ctcccagttc gcaagctcca    180
gtatgaatga gatcatcgac aagtacagca cmcattctaa gaacctgggg aaagcagacc    240
agccttctct tgacttgaay ttagaacata gtaagtatgc aaatctgaac gatcagcttg    300
cggaagctag tctycgactt agacagatga gaggcgaggg gcttgagggg ttgavtgttg    360
atgaactcca gcagttggag aagaaccttg aaactggtct gcacagggtg cttcagacga    420
aagatcaaca attcttggag cagatcaatg aattgcaacg aaagagctca cagctggcag    480
aggagaacat gcaactgagg aaccaagtat cccagatacc aatagctggc aagccagtag    540
ttgctgatac cgaaaatgtt attgctgagg atgggcagtc ctctgaatct gtcatgacgg    600
cgttgcactc gggaagcksa caggataacg atgatggttc agaygtatcc ctgaaattgg    660
gattacccctg cagtgcgtgg aag                                            683
```

<210> SEQ ID NO 11
<211> LENGTH: 447
<212> TYPE: DNA
<213> ORGANISM: Lolium perenne

<400> SEQUENCE: 11

```
gataccaata gctggcaagc cagtagttgc tgataccgaa aatgttattg ctgaggatgg      60
gcagtcctct gaatctgtca tgacggcgtt gcactcggga agcksacagg ataacgatga    120
tggttcagay gtatccctga aattgggatt accctgcagt gcgtggaagt aactatataa    180
aaycgtcrst tcagatcttt atggaactgc ccacrtcagt ggagaagctc ttgtgtaatc    240
sacaaacgta ccygagctgc aataatcttg crgctgaagc gagatcagtt aacctgattt    300
atcatccttg tggctgcatg acgtgatgtt mccgttytta cygtttacta ggatgttaac    360
taaacttttta gatcgatctg atgtccatct yatccccgtt grmactattw gttcatggta    420
wccatgtacc ttaactgtca gtatatc                                        447
```

```
<210> SEQ ID NO 12
<211> LENGTH: 228
<212> TYPE: PRT
<213> ORGANISM: Lolium perenne
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid

<400> SEQUENCE: 12

Met Ala Arg Glu Arg Glu Ile Lys Arg Ile Glu Ser Ala Ala Ala
1               5                   10                  15

Arg Gln Val Thr Phe Ser Lys Arg Arg Gly Leu Phe Lys Lys Ala
                20                  25                  30

Glu Glu Leu Ser Val Leu Cys Asp Ala Asp Val Ala Leu Ile Val Phe
            35                  40                  45

Ser Ser Thr Gly Lys Leu Ser Gln Phe Ala Ser Ser Ser Met Asn Glu
    50                  55                  60

Ile Ile Asp Lys Tyr Ser Thr His Ser Lys Asn Leu Gly Lys Ala Asp
65                  70                  75                  80

Gln Pro Ser Leu Asp Leu Asn Leu Glu His Ser Lys Tyr Ala Asn Leu
                85                  90                  95

Asn Asp Gln Leu Ala Glu Ala Ser Leu Arg Leu Arg Gln Met Arg Gly
            100                 105                 110

Glu Gly Leu Glu Gly Leu Xaa Val Asp Glu Leu Gln Gln Leu Glu Lys
        115                 120                 125

Asn Leu Glu Thr Gly Leu His Arg Val Leu Gln Thr Lys Asp Gln Gln
    130                 135                 140

Phe Leu Glu Gln Ile Asn Glu Leu Gln Arg Lys Ser Ser Gln Leu Ala
145                 150                 155                 160

Glu Glu Asn Met Gln Leu Arg Asn Gln Val Ser Gln Ile Pro Ile Ala
                165                 170                 175

Gly Lys Pro Val Val Ala Asp Thr Glu Asn Val Ile Ala Glu Asp Gly
            180                 185                 190

Gln Ser Glu Ser Val Met Thr Ala Leu His Ser Gly Ser Xaa Gln
        195                 200                 205

Asp Asn Asp Asp Gly Ser Asp Val Ser Leu Lys Leu Gly Leu Pro Cys
    210                 215                 220

Ser Ala Trp Lys
225

<210> SEQ ID NO 13
<211> LENGTH: 162
<212> TYPE: PRT
<213> ORGANISM: Arabidopsis thaliana

<400> SEQUENCE: 13

Asp Pro Leu Val Val Gly Arg Val Ile Gly Asp Val Leu Asp Met Phe
1               5                   10                  15

Ile Pro Thr Ala Asn Met Ser Val Tyr Phe Gly Pro Lys His Ile Thr
                20                  25                  30

Asn Gly Cys Glu Ile Lys Pro Ser Thr Ala Val Asn Pro Pro Lys Val
            35                  40                  45
```

-continued

```
Asn Ile Ser Gly His Ser Asp Glu Leu Tyr Thr Leu Val Met Thr Asp
 50                  55                  60

Pro Asp Ala Pro Ser Pro Ser Glu Pro Asn Met Arg Glu Trp Val His
 65                  70                  75                  80

Trp Ile Val Val Asp Ile Pro Gly Gly Thr Asn Pro Ser Arg Gly Lys
                 85                  90                  95

Glu Ile Leu Pro Tyr Met Glu Pro Arg Pro Val Gly Ile His Arg
            100                 105                 110

Tyr Ile Leu Val Leu Phe Arg Gln Asn Ser Pro Val Gly Leu Met Val
            115                 120                 125

Gln Gln Pro Pro Ser Arg Ala Asn Phe Ser Thr Arg Met Phe Ala Gly
130                 135                 140

His Phe Asp Leu Gly Leu Pro Val Ala Thr Val Tyr Phe Asn Ala Gln
145                 150                 155                 160

Lys Glu

<210> SEQ ID NO 14
<211> LENGTH: 174
<212> TYPE: PRT
<213> ORGANISM: Arabidopsis thaliana

<400> SEQUENCE: 14

Met Ser Ile Asn Ile Arg Asp Pro Leu Ile Val Ser Arg Val Val Gly
  1               5                  10                  15

Asp Val Leu Asp Pro Phe Asn Arg Ser Ile Thr Leu Lys Val Thr Tyr
                 20                  25                  30

Gly Gln Arg Glu Val Thr Asn Gly Leu Asp Leu Arg Pro Ser Gln Val
             35                  40                  45

Gln Asn Lys Pro Arg Val Glu Ile Gly Gly Glu Asp Leu Arg Asn Phe
 50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg
                165                 170

<210> SEQ ID NO 15
<211> LENGTH: 174
<212> TYPE: PRT
<213> ORGANISM: Arabidopsis thaliana

<400> SEQUENCE: 15

Met Ser Leu Ser Arg Arg Asp Pro Leu Val Val Gly Ser Val Val Gly
  1               5                  10                  15

Asp Val Leu Asp Pro Phe Thr Arg Leu Val Ser Leu Lys Val Thr Tyr
                 20                  25                  30

Gly His Arg Glu Val Thr Asn Gly Leu Asp Leu Arg Pro Ser Gln Val
```

```
            35                  40                  45
Leu Asn Lys Pro Ile Val Glu Ile Gly Gly Asp Asp Phe Arg Asn Phe
         50                  55                  60

Tyr Thr Leu Val Met Val Asp Pro Asp Val Pro Ser Pro Ser Asn Pro
 65                  70                  75                  80

His Gln Arg Glu Tyr Leu His Trp Leu Val Thr Asp Ile Pro Ala Thr
             85                  90                  95

Thr Gly Asn Ala Phe Gly Asn Glu Val Val Cys Tyr Glu Ser Pro Arg
            100                 105                 110

Pro Pro Ser Gly Ile His Arg Ile Val Leu Val Leu Phe Arg Gln Leu
        115                 120                 125

Gly Arg Gln Thr Val Tyr Ala Pro Gly Trp Arg Gln Gln Phe Asn Thr
130                 135                 140

Arg Glu Phe Ala Glu Ile Tyr Asn Leu Gly Leu Pro Val Ala Ala Ser
145                 150                 155                 160

Tyr Phe Asn Cys Gln Arg Glu Asn Gly Cys Gly Gly Arg Arg
                165                 170

<210> SEQ ID NO 16
<211> LENGTH: 171
<212> TYPE: PRT
<213> ORGANISM: Arabidopsis thaliana

<400> SEQUENCE: 16

Met Gly Thr Arg Val Ile Glu Pro Leu Ile Met Gly Arg Val Val Gly
 1                   5                  10                  15

Asp Val Leu Asp Phe Phe Thr Pro Thr Thr Lys Met Asn Val Ser Tyr
             20                  25                  30

Asn Lys Lys Gln Val Ser Asn Gly His Glu Leu Phe Pro Ser Ser Val
         35                  40                  45

Ser Ser Lys Pro Arg Val Glu Ile His Gly Gly Asp Leu Arg Ser Phe
     50                  55                  60

Phe Thr Leu Val Met Ile Asp Pro Asp Val Pro Gly Pro Ser Asp Pro
 65                  70                  75                  80

Phe Leu Lys Glu His Leu His Trp Ile Val Thr Asn Ile Pro Gly Thr
             85                  90                  95

Thr Asp Ala Thr Phe Gly Lys Glu Val Val Ser Tyr Glu Leu Pro Arg
            100                 105                 110

Pro Ser Ile Gly Ile His Arg Phe Val Phe Val Leu Phe Arg Gln Lys
        115                 120                 125

Gln Arg Arg Val Ile Phe Pro Asn Ile Pro Ser Arg Asp His Phe Asn
130                 135                 140

Thr Arg Lys Phe Ala Val Glu Tyr Asp Leu Gly Leu Pro Val Ala Ala
145                 150                 155                 160

Val Phe Phe Asn Ala Gln Arg Glu Thr Ala Ala
                165                 170

<210> SEQ ID NO 17
<211> LENGTH: 166
<212> TYPE: PRT
<213> ORGANISM: Arabidopsis thaliana

<400> SEQUENCE: 17

Asp Pro Leu Met Val Gly Arg Val Ile Gly Asp Val Val Asp Asn Cys
 1                   5                  10                  15

Leu Gln Ala Val Lys Met Thr Val Thr Tyr Asn Ser Asp Lys Gln Val
```

```
            20                  25                  30
Tyr Asn Gly His Glu Leu Phe Pro Ser Val Val Thr Tyr Lys Pro Lys
        35                  40                  45

Val Glu Val His Gly Gly Asp Met Arg Ser Phe Phe Thr Leu Val Met
 50                  55                  60

Thr Asp Pro Asp Val Pro Gly Pro Ser Asp Pro Tyr Leu Arg Glu His
 65                  70                  75                  80

Leu His Trp Ile Val Thr Asp Ile Pro Gly Thr Thr Asp Val Ser Phe
                 85                  90                  95

Gly Lys Glu Ile Ile Gly Tyr Glu Met Pro Arg Pro Asn Ile Gly Ile
            100                 105                 110

His Arg Phe Val Tyr Leu Leu Phe Lys Gln Thr Arg Arg Gly Ser Val
        115                 120                 125

Val Ser Val Pro Ser Tyr Arg Asp Gln Phe Asn Thr Arg Glu Phe Ala
    130                 135                 140

His Glu Asn Asp Leu Gly Leu Pro Val Ala Ala Val Phe Phe Asn Cys
145                 150                 155                 160

Gln Arg Glu Thr Ala Ala
                165

<210> SEQ ID NO 18
<211> LENGTH: 165
<212> TYPE: PRT
<213> ORGANISM: Lolium perenne

<400> SEQUENCE: 18

Glu Pro Leu Ile Val Gly Arg Val Ile Gly Glu Val Leu Asp Pro Phe
  1               5                  10                  15

Asn Pro Cys Val Lys Met Val Ala Thr Tyr Asn Ser Asn Lys Leu Val
             20                  25                  30

Phe Asn Gly His Glu Leu Tyr Pro Ser Ala Val Val Ser Lys Pro Arg
        35                  40                  45

Val Glu Val Gln Gly Gly Asp Leu Arg Ser Leu Phe Thr Leu Val Met
 50                  55                  60

Ala Asp Pro Asp Val Pro Gly Pro Ser Asp Pro Tyr Leu Arg Glu His
 65                  70                  75                  80

Leu His Trp Ile Val Ser Asn Ile Pro Gly Thr Thr Asp Ala Ser Phe
                 85                  90                  95

Gly Gly Glu Val Met Ser Tyr Glu Ser Pro Lys Pro Asn Ile Gly Ile
            100                 105                 110

His Arg Phe Ile Phe Val Leu Phe Lys Gln Lys Arg Arg Gln Thr Val
        115                 120                 125

Ser Val Pro Ser Phe Arg Asp His Phe Asn Thr Arg Gln Phe Ala Val
    130                 135                 140

Asp Asn Asp Leu Gly Leu Pro Val Ala Ala Val Tyr Phe Asn Cys Gln
145                 150                 155                 160

Arg Glu Thr Ala Ala
                165

<210> SEQ ID NO 19
<211> LENGTH: 164
<212> TYPE: PRT
<213> ORGANISM: Arabidopsis thaliana

<400> SEQUENCE: 19

Glu Pro Leu Ile Val Gly Arg Val Ile Gly Asp Val Leu Glu Met Phe
```

-continued

```
              1               5                  10                 15
        Asn Pro Ser Val Thr Met Arg Val Thr Phe Asn Ser Asn Thr Ile Val
                        20                 25                 30

Ser Asn Gly His Glu Leu Ala Pro Ser Leu Leu Ser Lys Pro Arg
                   35                 40                 45

Val Glu Ile Gly Gly Gln Asp Leu Arg Ser Phe Phe Thr Leu Ile Met
                   50                 55                 60

Met Asp Pro Asp Ala Pro Ser Pro Ser Asn Pro Tyr Met Arg Glu Tyr
         65                 70                 75                 80

Leu His Trp Met Val Thr Asp Ile Pro Gly Thr Thr Asp Ala Ser Phe
                        85                 90                 95

Gly Arg Glu Ile Val Arg Tyr Glu Thr Pro Lys Pro Val Ala Gly Ile
                       100                105                110

His Arg Tyr Val Phe Ala Leu Phe Lys Gln Arg Gly Arg Gln Ala Val
                       115                120                125

Lys Ala Ala Pro Glu Thr Arg Glu Cys Phe Asn Thr Asn Ala Phe Ser
            130                135                140

Ser Tyr Phe Gly Leu Ser Gln Pro Val Ala Ala Val Tyr Phe Asn Ala
        145                150                155                160

Gln Arg Glu Thr
```

<210> SEQ ID NO 20
<211> LENGTH: 72
<212> TYPE: PRT
<213> ORGANISM: Lolium perenne

<400> SEQUENCE: 20

```
        Val Leu Tyr Leu Arg Pro Gln Pro Val Gly Ile His Arg Tyr Val
        1               5                  10                 15

Leu Val Leu Phe Gln Gln Lys Ser Arg Ile Val Asp Gly Tyr Ala Ala
                       20                 25                 30

Pro Pro Ala Asp Arg Pro Tyr Phe Asn Thr Arg Ala Phe Ala Phe Asn
                       35                 40                 45

His Glu Leu Gly Leu Pro Val Ala Val Val Tyr Phe Asn Ser Gln Arg
            50                 55                 60

Glu Pro Ser Gly Asn Arg Arg Arg
        65                 70
```

<210> SEQ ID NO 21
<211> LENGTH: 77
<212> TYPE: PRT
<213> ORGANISM: Lolium perenne

<400> SEQUENCE: 21

```
        Val Ser Phe Gly Thr Glu Val Val Cys Tyr Glu Ser Pro Arg Pro Val
        1               5                  10                 15

Leu Gly Ile His Arg Leu Val Phe Leu Leu Phe Gln Gln Leu Gly Arg
                       20                 25                 30

Gln Thr Val Tyr Ala Pro Gly Trp Arg Gln Asn Phe Ser Thr Arg Asp
                       35                 40                 45

Phe Ala Glu Leu Tyr Asn Leu Gly Ser Pro Val Ala Ala Val Tyr Phe
            50                 55                 60

Asn Cys Gln Arg Glu Ser Gly Thr Gly Gly Arg Arg Met
        65                 70                 75
```

<210> SEQ ID NO 22

```
<211> LENGTH: 77
<212> TYPE: PRT
<213> ORGANISM: Lolium perenne

<400> SEQUENCE: 22

Val Ser Phe Gly Thr Glu Val Val Cys Tyr Glu Ser Pro Arg Pro Val
1               5                   10                  15

Leu Gly Ile His Arg Leu Val Phe Leu Leu Phe Gln Gln Leu Gly Arg
            20                  25                  30

Gln Thr Val Tyr Ala Pro Gly Trp Arg Gln Asn Phe Ser Thr Arg Asp
        35                  40                  45

Phe Ala Glu Leu Tyr Asn Leu Gly Ser Pro Val Ala Ala Val Tyr Phe
    50                  55                  60

Asn Cys Gln Arg Glu Ser Gly Thr Gly Gly Arg Arg Met
65                  70                  75

<210> SEQ ID NO 23
<211> LENGTH: 170
<212> TYPE: PRT
<213> ORGANISM: Lolium perenne

<400> SEQUENCE: 23

Met Ala Arg Val Val Glu Pro Leu Ile Val Gly Lys Val Ile Gly Glu
1               5                   10                  15

Val Ile Asp Asn Phe Thr Pro Thr Glu Lys Met Thr Val Thr Tyr Ser
            20                  25                  30

Ser Asn Lys Gln Val Phe Asn Gly His Glu Phe Phe Pro Ser Ala Val
        35                  40                  45

Val Ser Lys Pro Arg Ile Glu Val Gln Gly Gly Asp Met Arg Ser Phe
    50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Asn Asn Ile Pro Gly Thr
                85                  90                  95

Thr Asp Ala Ser Phe Gly Lys Glu Val Val Ser Tyr Glu Ser Pro Lys
            100                 105                 110

Pro Asn Ile Gly Ile His Arg Phe Thr Phe Val Leu Phe Lys Gln Lys
        115                 120                 125

Gln Arg Gln Thr Met Ser Pro Pro Ser Ser Arg Asp Tyr Phe Asn Thr
    130                 135                 140

Arg Arg Phe Ala Ala Ala Asn Asp Leu Gly Leu Pro Val Ala Ala Val
145                 150                 155                 160

Tyr Phe Asn Ala Gln Arg Glu Thr Ala Ala
                165                 170

<210> SEQ ID NO 24
<211> LENGTH: 171
<212> TYPE: PRT
<213> ORGANISM: Lolium perenne

<400> SEQUENCE: 24

Met Ser Arg Ala Leu Glu Pro Leu Val Val Gly Lys Val Ile Gly Glu
1               5                   10                  15

Val Leu Asp Ser Phe Asn Pro Thr Val Lys Met Thr Ala Thr Tyr Ser
            20                  25                  30

Ser Asn Lys Gln Val Phe Asn Gly His Glu Phe Phe Pro Ser Ala Ile
        35                  40                  45
```

```
Ala Ala Lys Pro Arg Val Glu Val Gln Gly Gly Asp Leu Arg Ser Phe
    50                  55                  60

Phe Thr Leu Val Met Thr Asp Pro Asp Val Pro Gly Pro Ser Asp Pro
 65                  70                  75                  80

Tyr Leu Arg Glu His Leu His Trp Ile Val Thr Asp Ile Pro Gly Thr
                 85                  90                  95

Thr Asp Ala Ser Phe Gly Lys Glu Val Val His Tyr Glu Ser Pro Lys
            100                 105                 110

Pro Asn Ile Gly Ile His Arg Phe Ile Leu Val Leu Phe Gln Gln Thr
            115                 120                 125

His Arg Gly Ser Val Lys Asn Thr Pro Ser Ser Arg Asp Arg Phe Arg
    130                 135                 140

Thr Arg Glu Phe Ala Lys Asp Asn Glu Leu Gly Leu Pro Val Ala Ala
145                 150                 155                 160

Val Tyr Phe Asn Ala Gln Arg Glu Thr Ala Ala
                165                 170
```

```
<210> SEQ ID NO 25
<211> LENGTH: 120
<212> TYPE: PRT
<213> ORGANISM: Lolium perenne

<400> SEQUENCE: 25

Met Thr Asp Pro Ala Ala Pro Ser Arg Lys Glu Pro Lys Phe Arg Glu
 1               5                  10                  15

Trp His His Trp Leu Val Gly Asn Val Pro Glu Cys Asp Val Ala Lys
                 20                  25                  30

Gly Glu Thr Leu Ser Glu Tyr Ile Gly Ser Gly Pro Pro Asp Thr
            35                  40                  45

Gly Leu His Arg Tyr Val Phe Leu Val Tyr Leu Gln Pro Gly Lys Ile
    50                  55                  60

Asp Phe Lys Asp Val Pro Arg Leu Thr Asn Arg Ser Gly Asp Asn Arg
 65                  70                  75                  80

Ala Asn Phe Lys Ile Gln Ala Phe Ala Asp Lys Tyr Asn Leu Gly Asp
                 85                  90                  95

Pro Val Ala Ser Ala Tyr Tyr Arg Ala Glu Tyr Asp Tyr Val Pro
            100                 105                 110

Ile Leu Tyr Lys Gln Leu Gly Ala
            115                 120
```

```
<210> SEQ ID NO 26
<211> LENGTH: 176
<212> TYPE: PRT
<213> ORGANISM: Oryza sativa

<400> SEQUENCE: 26

Met Ser Gly Arg Gly Arg Gly Asp Pro Leu Val Leu Gly Arg Val Val
 1               5                  10                  15

Gly Asp Val Val Asp Pro Phe Val Arg Arg Val Ala Leu Arg Val Ala
                 20                  25                  30

Tyr Gly Ala Arg Glu Val Ala Asn Gly Cys Glu Leu Arg Pro Ser Ala
            35                  40                  45

Val Ala Asp Gln Pro Arg Val Ala Val Gly Gly Pro Asp Met Arg Thr
    50                  55                  60

Phe Tyr Thr Leu Val Met Val Asp Pro Asp Ala Pro Ser Pro Ser Asp
 65                  70                  75                  80
```

```
Pro Asn Leu Arg Glu Tyr Leu His Trp Leu Val Thr Asp Ile Pro Ala
                85                  90                  95

Thr Thr Gly Val Ser Phe Gly Thr Glu Val Val Cys Tyr Glu Ser Pro
            100                 105                 110

Arg Pro Val Leu Gly Ile His Arg Leu Val Phe Leu Leu Phe Glu Gln
        115                 120                 125

Leu Gly Arg Gln Thr Val Tyr Ala Pro Gly Trp Arg Gln Asn Phe Ser
    130                 135                 140

Thr Arg Asp Phe Ala Glu Leu Tyr Asn Leu Gly Leu Pro Val Ala Ala
145                 150                 155                 160

Val Tyr Phe Asn Cys Gln Arg Glu Ser Gly Thr Gly Gly Arg Arg Met
                165                 170                 175

<210> SEQ ID NO 27
<211> LENGTH: 178
<212> TYPE: PRT
<213> ORGANISM: Oryza sativa

<400> SEQUENCE: 27

Met Ser Gly Val Pro Thr Val Glu Pro Leu Val Leu Ala His Val Ile
1               5                   10                  15

His Asp Val Leu Asp Pro Phe Arg Pro Thr Met Pro Leu Arg Ile Thr
                20                  25                  30

Tyr Asn Asp Arg Leu Leu Leu Ala Gly Ala Glu Leu Lys Pro Ser Ala
            35                  40                  45

Thr Val His Lys Pro Arg Val Asp Ile Gly Gly Thr Asp Leu Arg Val
        50                  55                  60

Phe Tyr Thr Leu Val Leu Val Asp Pro Asp Ala Pro Ser Pro Ser Asn
65                  70                  75                  80

Pro Ser Leu Gly Glu Tyr Leu His Met Val Ile Asp Ile Pro Gly Thr
                85                  90                  95

Thr Gly Val Asn Cys Gln Asp Leu Met Leu Tyr Glu Arg Pro Glu Leu
            100                 105                 110

Arg Tyr Gly Ile His Arg Met Val Phe Val Leu Phe Arg Gln Leu Gly
        115                 120                 125

Arg Gly Thr Val Phe Ala Pro Glu Met Arg His Asn Phe His Cys Arg
    130                 135                 140

Ser Phe Ala Gln Gln Tyr His Leu Asp Ile Val Ala Ala Thr Tyr Phe
145                 150                 155                 160

Asn Cys Gln Arg Glu Ala Gly Ser Gly Gly Arg Arg Phe Arg Ser Glu
                165                 170                 175

Ser Ser

<210> SEQ ID NO 28
<211> LENGTH: 170
<212> TYPE: PRT
<213> ORGANISM: Lolium perenne

<400> SEQUENCE: 28

Met Ser Arg Ser Val Glu Pro Leu Ile Val Gly Arg Val Ile Gly Glu
1               5                   10                  15

Val Leu Asp Pro Phe Asn Pro Cys Val Lys Met Val Ala Thr Tyr Asn
                20                  25                  30

Ser Asn Lys Leu Val Phe Asn Gly His Glu Leu Tyr Pro Ser Ala Val
            35                  40                  45

Val Ser Lys Pro Arg Val Glu Val Gln Gly Gly Asp Leu Arg Ser Leu
```

```
            50                  55                  60
Phe Thr Leu Val Met Thr Asp Pro Asp Val Pro Gly Pro Ser Asp Pro
 65                  70                  75                  80

Tyr Leu Arg Glu His Leu His Trp Ile Val Ser Asn Ile Pro Gly Thr
                 85                  90                  95

Thr Asp Ala Ser Phe Gly Gly Glu Val Met Ser Tyr Glu Ser Pro Lys
                100                 105                 110

Pro Asn Ile Gly Ile His Arg Phe Ile Phe Val Leu Phe Lys Gln Lys
            115                 120                 125

Arg Arg Gln Thr Val Ser Val Pro Ser Phe Arg Asp His Phe Asn Thr
130                 135                 140

Arg Gln Phe Ala Val Asp Asn Asp Leu Gly Leu Pro Val Ala Ala Val
145                 150                 155                 160

Tyr Phe Asn Cys Gln Arg Glu Thr Ala Ala
                165                 170
```

<210> SEQ ID NO 29
<211> LENGTH: 170
<212> TYPE: PRT
<213> ORGANISM: Oryza sativa

<400> SEQUENCE: 29

```
Met Ser Arg Ser Val Glu Pro Leu Val Gly Arg Val Ile Gly Glu
 1               5                  10                  15

Val Ile Asp Ser Phe Asn Pro Cys Thr Lys Met Ile Val Thr Tyr Asn
                20                  25                  30

Ser Asn Lys Leu Val Phe Asn Gly His Glu Phe Tyr Pro Ser Ala Val
             35                  40                  45

Val Ser Lys Pro Arg Val Glu Val Gln Gly Gly Asp Met Arg Ser Phe
 50                  55                  60

Phe Thr Leu Val Met Thr Asp Pro Asp Val Pro Gly Pro Ser Asp Pro
 65                  70                  75                  80

Tyr Leu Arg Glu His Leu His Trp Ile Val Thr Asp Ile Pro Gly Thr
                 85                  90                  95

Thr Asp Ala Ser Phe Gly Arg Glu Ile Ile Ser Tyr Glu Ser Pro Lys
                100                 105                 110

Pro Ser Ile Gly Ile His Arg Phe Val Phe Val Leu Phe Lys Gln Lys
            115                 120                 125

Arg Arg Gln Ala Val Val Val Pro Ser Ser Arg Asp His Phe Asn Thr
130                 135                 140

Arg Gln Phe Ala Glu Glu Asn Glu Leu Gly Leu Pro Val Ala Ala Val
145                 150                 155                 160

Tyr Phe Asn Ala Gln Arg Glu Thr Ala Ala
                165                 170
```

<210> SEQ ID NO 30
<211> LENGTH: 178
<212> TYPE: PRT
<213> ORGANISM: Oryza sativa

<400> SEQUENCE: 30

```
Met Ala Gly Ser Gly Arg Asp Asp Pro Leu Val Val Gly Arg Ile Val
 1               5                  10                  15

Gly Asp Val Leu Asp Pro Phe Val Arg Ile Thr Asn Leu Ser Val Ser
                20                  25                  30

Tyr Gly Ala Arg Ile Val Ser Asn Gly Cys Glu Leu Lys Pro Ser Met
```

```
                35                  40                  45
Val Thr Gln Gln Pro Arg Val Val Gly Gly Asn Asp Met Arg Thr
 50                  55                  60
Phe Tyr Thr Leu Val Met Val Asp Pro Asp Ala Pro Ser Pro Ser Asn
65                  70                  75                  80
Pro Asn Leu Arg Glu Tyr Leu His Trp Leu Val Thr Asp Ile Pro Gly
                85                  90                  95
Thr Thr Gly Ala Thr Phe Gly Gln Glu Val Met Cys Tyr Glu Ser Pro
                100                 105                 110
Arg Pro Thr Met Gly Ile His Arg Leu Val Phe Val Leu Phe Gln Gln
                115                 120                 125
Leu Gly Arg Gln Thr Val Tyr Ala Pro Gly Trp Arg Gln Asn Phe Ser
130                 135                 140
Thr Arg Asn Phe Ala Glu Leu Tyr Asn Leu Gly Ser Pro Val Ala Thr
145                 150                 155                 160
Val Tyr Phe Asn Cys Gln Arg Glu Ala Gly Ser Gly Gly Arg Arg Val
                165                 170                 175
Tyr Pro

<210> SEQ ID NO 31
<211> LENGTH: 180
<212> TYPE: PRT
<213> ORGANISM: Oryza sativa

<400> SEQUENCE: 31

Met Ser Ser Ala Asn Ser Leu Val Leu Gly Arg Val Ile Gly Asp Val
1               5                   10                  15
Val Asp Leu Phe Ser Pro Glu Val Thr Leu Arg Val Met Tyr Asn Gly
                20                  25                  30
Val Arg Val Val Asn Gly Glu Asp Leu Arg Pro Ser Ala Val Ser Ala
                35                  40                  45
Arg Pro Ser Val Glu Val Gly Gly Asp Leu His Gln Phe Tyr Thr Ile
 50                  55                  60
Val Met Val Asp Pro Asp Ala Pro Asn Pro Ser Asn Pro Thr Leu Arg
65                  70                  75                  80
Glu Tyr Leu His Trp Leu Val Thr Asp Ile Pro Gly Thr Thr Asp Ala
                85                  90                  95
Asn Tyr Gly Arg Glu Val Val Cys Tyr Glu Ser Pro Arg Pro Ala Ala
                100                 105                 110
Gly Ile His Arg Val Ala Val Val Leu Phe Arg Gln Met Ala Arg Gly
                115                 120                 125
Gly Val Asp Gln Pro Pro Leu Leu Arg His Asn Phe Ser Thr Arg Gly
130                 135                 140
Phe Ala Asp Asp His Ala Leu Gly Ala Pro Val Ala Ala Ala Phe Phe
145                 150                 155                 160
Thr Cys Lys Pro Glu Gly Gly Thr Gly Gly Arg Arg Phe Arg Pro Pro
                165                 170                 175
Ser Arg His Ser
                180

<210> SEQ ID NO 32
<211> LENGTH: 173
<212> TYPE: PRT
<213> ORGANISM: Oryza sativa

<400> SEQUENCE: 32
```

Met Ser Arg Ser Val Glu Pro Leu Val Val Gly Arg Val Ile Gly Glu
1               5                   10                  15

Val Leu Asp Thr Phe Asn Pro Cys Met Lys Met Ile Val Thr Tyr Asn
            20                  25                  30

Ser Asn Lys Leu Val Phe Asn Gly His Glu Leu Tyr Pro Ser Ala Val
            35                  40                  45

Val Ser Lys Pro Arg Val Glu Val Gln Gly Gly Asp Leu Arg Ser Phe
        50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Ser Phe Gly Arg Glu Val Ile Ser Tyr Glu Ser Pro Lys
                100                 105                 110

Pro Asn Ile Gly Ile His Arg Phe Ile Phe Val Leu Phe Lys Gln Lys
                115                 120                 125

Arg Arg Gln Thr Val Ile Val Pro Ser Phe Arg Asp His Phe Asn Thr
            130                 135                 140

Arg Arg Phe Ala Glu Glu Asn Asp Leu Gly Leu Pro Val Ala Ala Val
145                 150                 155                 160

Tyr Phe Asn Ala Gln Arg Glu Thr Ala Ala Arg Arg Arg
                165                 170

<210> SEQ ID NO 33
<211> LENGTH: 174
<212> TYPE: PRT
<213> ORGANISM: Oryza sativa

<400> SEQUENCE: 33

Met Ala Arg Phe Val Asp Pro Leu Val Val Gly Arg Val Ile Gly Glu
1               5                   10                  15

Val Val Asp Leu Phe Val Pro Ser Ile Ser Met Thr Ala Ala Tyr Gly
            20                  25                  30

Asp Arg Asp Ile Ser Asn Gly Cys Leu Val Arg Pro Ser Ala Ala Asp
            35                  40                  45

Tyr Pro Pro Leu Val Arg Ile Ser Gly Arg Arg Asn Asp Leu Tyr Thr
        50                  55                  60

Leu Ile Met Thr Asp Pro Asp Ala Pro Ser Pro Ser Asp Pro Ser Met
65                  70                  75                  80

Arg Glu Phe Leu His Trp Ile Val Asn Ile Pro Gly Gly Thr Asp Ala
                85                  90                  95

Ser Lys Gly Glu Glu Met Val Glu Tyr Met Gly Pro Arg Pro Thr
100                 105                 110

Val Gly Ile His Arg Tyr Val Leu Val Leu Tyr Glu Gln Lys Ala Arg
            115                 120                 125

Phe Val Asp Gly Ala Leu Met Pro Pro Ala Asp Arg Pro Asn Phe Asn
        130                 135                 140

Thr Arg Ala Phe Ala Ala Tyr His Gln Leu Gly Leu Pro Thr Ala Val
145                 150                 155                 160

Val His Phe Asn Ser Gln Arg Glu Pro Ala Asn Arg Arg Arg
                165                 170

<210> SEQ ID NO 34
<211> LENGTH: 173
<212> TYPE: PRT

-continued

<213> ORGANISM: Oryza sativa

<400> SEQUENCE: 34

Met Ser Arg Val Leu Glu Pro Leu Val Val Gly Lys Val Ile Gly Glu
1               5                   10                  15

Val Ile Asp Asn Phe Asn Pro Thr Val Lys Met Thr Ala Thr Tyr Ser
            20                  25                  30

Ser Asn Lys Gln Val Phe Asn Gly His Glu Leu Phe Pro Ser Ala Val
        35                  40                  45

Val Ser Lys Pro Arg Val Glu Val Gln Gly Gly Asp Leu Arg Ser Phe
    50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Ser Phe Gly Arg Glu Val Val Ser Tyr Glu Ser Pro Lys
            100                 105                 110

Pro Asn Ile Gly Ile His Arg Phe Val Leu Val Leu Phe Lys Gln Lys
        115                 120                 125

Arg Arg Gln Ala Val Thr Pro Pro Ser Ser Arg Asp Tyr Phe Ser Thr
    130                 135                 140

Arg Arg Phe Ala Ala Asp Asn Asp Leu Gly Leu Pro Val Ala Ala Val
145                 150                 155                 160

Tyr Phe Asn Ala Gln Arg Glu Thr Ala Ala Arg Arg Arg
                165                 170

<210> SEQ ID NO 35
<211> LENGTH: 185
<212> TYPE: PRT
<213> ORGANISM: Oryza sativa

<400> SEQUENCE: 35

Met Ala Asn Asp Ser Leu Ala Thr Gly Arg Val Ile Gly Asp Val Leu
1               5                   10                  15

Asp Pro Phe Ile Ser Thr Val Asp Leu Thr Val Met Tyr Gly Asp Asp
            20                  25                  30

Gly Met Pro Val Ile Ser Gly Val Glu Leu Arg Ala Pro Ala Val Ala
        35                  40                  45

Glu Lys Pro Val Val Glu Val Gly Gly Asp Asp Leu Arg Val Ala Tyr
    50                  55                  60

Thr Leu Val Met Val Asp Pro Asp Ala Pro Asn Pro Ser Asn Pro Thr
65                  70                  75                  80

Leu Arg Glu Tyr Leu His Trp Met Val Thr Asp Ile Pro Ala Ser Thr
                85                  90                  95

Asp Ala Thr Tyr Gly Arg Glu Val Val Cys Tyr Glu Ser Pro Asn Pro
            100                 105                 110

Thr Thr Gly Ile His Arg Met Val Leu Val Leu Phe Arg Gln Leu Gly
        115                 120                 125

Arg Glu Thr Val Tyr Ala Pro Ala Val Arg His Asn Phe Thr Thr Arg
    130                 135                 140

Ala Phe Ala Arg Arg Tyr Asn Leu Gly Ala Pro Val Ala Ala Val Tyr
145                 150                 155                 160

Phe Asn Cys Gln Arg Gln Ala Gly Ser Gly Arg Arg Phe Thr Gly
                165                 170                 175

Pro Tyr Thr Ser Arg Arg Arg Gln Ala

```
                180             185

<210> SEQ ID NO 36
<211> LENGTH: 179
<212> TYPE: PRT
<213> ORGANISM: Oryza sativa

<400> SEQUENCE: 36

Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
    130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Pro

<210> SEQ ID NO 37
<211> LENGTH: 177
<212> TYPE: PRT
<213> ORGANISM: Lolium perenne

<400> SEQUENCE: 37

Met Ala Gly Arg Asp Arg Asp Pro Leu Val Val Gly Arg Val Val Gly
1               5                   10                  15

Asp Val Leu Asp Pro Phe Ile Arg Thr Thr Asn Leu Arg Val Thr Phe
            20                  25                  30

Gly Asn Arg Ala Val Ser Asn Gly Cys Glu Leu Lys Pro Ser Met Val
        35                  40                  45

Thr His Gln Pro Arg Val Glu Val Gly Gly Asn Asp Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Asn Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140
```

```
Arg Asp Phe Ala Glu Leu Tyr Asn Leu Gly Pro Pro Val Ala Ala Val
145                 150                 155                 160

Tyr Phe Asn Cys Gln Arg Glu Ala Gly Ser Gly Asp Arg Arg Met Tyr
                165                 170                 175

Asn

<210> SEQ ID NO 38
<211> LENGTH: 177
<212> TYPE: PRT
<213> ORGANISM: Lolium perenne

<400> SEQUENCE: 38

Met Ala Gly Arg Asp Arg Asp Pro Leu Val Val Gly Arg Val Val Gly
1               5                   10                  15

Asp Val Leu Asp Pro Phe Ile Arg Thr Thr Asn Leu Arg Val Thr Phe
            20                  25                  30

Gly Asn Arg Ala Val Ser Asn Gly Cys Glu Leu Lys Pro Ser Met Val
        35                  40                  45

Thr His Gln Pro Arg Val Glu Val Gly Gly Asn Asp Met Arg Thr Phe
    50                  55                  60

Tyr Thr Leu Val Met Val Asp Pro Asp Ala Pro Ser Pro Ser Asp Pro
65                  70                  75                  80

Ser Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Asn Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Pro Pro Val Ala Ala Val
145                 150                 155                 160

Tyr Phe Asn Cys Gln Arg Glu Ala Gly Ser Gly Asp Arg Arg Met Tyr
                165                 170                 175

Asn

<210> SEQ ID NO 39
<211> LENGTH: 26
<212> TYPE: DNA
<213> ORGANISM: Lolium perenne

<400> SEQUENCE: 39
tgatgcatgt catgaaggca atgaag                                      26

<210> SEQ ID NO 40
<211> LENGTH: 14
<212> TYPE: DNA
<213> ORGANISM: Lolium perenne

<400> SEQUENCE: 40
caatgtctgt tccc                                                   14

<210> SEQ ID NO 41
<211> LENGTH: 21
<212> TYPE: DNA
<213> ORGANISM: Lolium perenne

<400> SEQUENCE: 41
```

```
<210> SEQ ID NO 42
<211> LENGTH: 14
<212> TYPE: DNA
<213> ORGANISM: Lolium perenne

<400> SEQUENCE: 42
acaaagcaaa aaat                                                        14

<210> SEQ ID NO 43
<211> LENGTH: 20
<212> TYPE: DNA
<213> ORGANISM: Artificial
<220> FEATURE:
<223> OTHER INFORMATION: synthetic primer

<400> SEQUENCE: 43
catgaaatgt gcagaacagg                                                  20

<210> SEQ ID NO 44
<211> LENGTH: 21
<212> TYPE: DNA
<213> ORGANISM: Artificial
<220> FEATURE:
<223> OTHER INFORMATION: synthetic primer

<400> SEQUENCE: 44
tggttgactc tccacatctt c                                                21

<210> SEQ ID NO 45
<211> LENGTH: 23
<212> TYPE: DNA
<213> ORGANISM: Artificial
<220> FEATURE:
<223> OTHER INFORMATION: synthetic primer

<400> SEQUENCE: 45
gctgttttcc ctagcattgt tgg                                              23

<210> SEQ ID NO 46
<211> LENGTH: 23
<212> TYPE: DNA
<213> ORGANISM: Artificial
<220> FEATURE:
<223> OTHER INFORMATION: synthetic primer

<400> SEQUENCE: 46
ataagagaat ccgtgagatc ccg                                              23
```
cgtgaggaaa tgaacaacag a                                                21